United States Patent
Kiyohara et al.

(10) Patent No.: US 9,025,725 B2
(45) Date of Patent: May 5, 2015

(54) X-RAY IMAGE CAPTURING APPARATUS, X-RAY IMAGING SYSTEM AND X-RAY IMAGE CREATION METHOD

(75) Inventors: Junko Kiyohara, Hino (JP); Kazuhiro Kido, Hino (JP); Chiho Makifuchi, Hino (JP)

(73) Assignee: Konica Minolta Medical & Graphic, Inc. (JP)

( * ) Notice: Subject to any disclaimer, the term of this patent is extended or adjusted under 35 U.S.C. 154(b) by 354 days.

(21) Appl. No.: 13/394,862

(22) PCT Filed: Mar. 10, 2010

(86) PCT No.: PCT/JP2010/053978
§ 371 (c)(1),
(2), (4) Date: Mar. 8, 2012

(87) PCT Pub. No.: WO2011/033798
PCT Pub. Date: Mar. 24, 2011

(65) Prior Publication Data
US 2012/0224670 A1   Sep. 6, 2012

(30) Foreign Application Priority Data

Sep. 16, 2009   (JP) ................................ 2009-214483

(51) Int. Cl.
*G01N 23/04* (2006.01)
*A61B 6/06* (2006.01)
*A61B 6/00* (2006.01)
*A61B 6/04* (2006.01)

(52) U.S. Cl.
CPC .............. *G01N 23/04* (2013.01); *A61B 6/0457* (2013.01); *A61B 6/06* (2013.01); *A61B 6/484* (2013.01); *A61B 6/4291* (2013.01); *G21K 2207/005* (2013.01)

(58) Field of Classification Search
USPC ............ 378/36, 62, 147, 149, 154, 155, 98.8, 378/193, 195, 196, 197
See application file for complete search history.

(56) References Cited

U.S. PATENT DOCUMENTS 7,889,838 B2 *  2/2011  David et al. ...................... 378/36
8,411,816 B2 *  4/2013  Ohara ............................. 378/36

FOREIGN PATENT DOCUMENTS

| JP | 58-016216 A | 1/1983 |
| JP | 2007-203063 A | 8/2007 |
| JP | 2007-268033 A | 10/2007 |
| JP | 2008-018060 A | 1/2008 |
| JP | 2009-150875 A | 7/2009 |
| WO | 2004/058070 A1 | 7/2004 |
| WO | 2008/102685 A1 | 8/2008 |

OTHER PUBLICATIONS

International Search Report for International application No. PCT/JP2010/053978 mailing date of Apr. 13, 2010.

* cited by examiner

*Primary Examiner* — Jurie Yun
(74) *Attorney, Agent, or Firm* — Cantor Colburn LLP

(57) ABSTRACT

The apparatus includes: an X-ray source a multi slits element a first grating; a second grating; a driving section; a subject placing plate: and an X-ray detector, in which conversion elements to convert intensities of X-rays received thereby to electric signals, are arranged in a two-dimensional pattern so as to read the electric signals as image signals. The driving section moves the multi slits element relative to both the first grating and the second grating in a first direction orthogonal to a second direction of irradiating the X-rays, so that the X-ray detector repeats a processing for reading the electric signals converted from the intensities of X-rays received thereby, every time when the multi slits element moves at predetermined intervals so as to acquire the image signals representing Moire images captured at the predetermined intervals.

9 Claims, 10 Drawing Sheets

○ VALUES WHEN MOVING AMOUNT IS CONSTANT
● VALUES WHEN MOVING AMOUNTS ARE DEVIATED FROM EACH OTHER

FIRST STEP  SECOND STEP  THIRD STEP  FOURTH STEP  FIFTH STEP

FIRST STEP  SECOND STEP  THIRD STEP  FOURTH STEP  FIFTH STEP

FIRST STEP  SECOND STEP  THIRD STEP  FOURTH STEP  FIFTH STEP

FIRST STEP  SECOND STEP  THIRD STEP  FOURTH STEP  FIFTH STEP

222: APERTURE SECTION

223

221

- - - - - - X-RAY IRRADIATION AREA

X-RAY IMAGE CAPTURING APPARATUS, X-RAY IMAGING SYSTEM AND X-RAY IMAGE CREATION METHOD

This application is based on Japanese Patent Application NO. 2009-214483 filed on Sep. 16, 2009, with the Japan Patent Office, the entire content of which is hereby incorporated by reference.

BACKGROUND OF THE INVENTION

The present invention relates to an X-ray image capturing apparatus, an X-ray imaging system and an X-ray image creation method.

Conventionally, almost of all X-ray images to be used for diagnosis purpose have been acquired by employing the absorption-contrast X-ray method. According to the absorption-contrast X-ray method, contrasts in an X-ray image are formed corresponding to differences between X-ray intensities generated after X-rays have penetrated through the subject. On the other hand, instead of employing the X-ray absorbing action, the phase-contrast method has been proposed as another method for acquiring the contrasts in the X-ray image, which employs the X-ray phase change action. For instance, there has been put in practice such a phase-contrast image capturing operation that acquires an X-ray image having a high visibility by employing the edge enhancement processing, which utilize the X-ray refraction at the time of an enlarged image capturing operation, as set forth in, for instance, Tokkai 2007-268033 and Tokkai 2008-18060 (both are Japanese Patent Application Laid-Open Publications).

The absorption-contrast X-ray method is effective for capturing an X-ray image of such a subject that has a relatively large X-ray absorption rate, such as a born, etc. In contrast, according to the phase-contrast X-ray method, it is possible to visualize even such soft tissue portions, such as a breast tissue, a cartilage of a joint, a soft tissue around a joint, images of which are hardly acquired by employing the absorption-contrast X-ray method, due to the small X-ray absorption rate. Accordingly, it is expected to widely introduce the phase-contrast X-ray method into the X-ray image diagnosing field.

As one of the radiographic image capturing apparatus employing the phase-contrast method, it has been considered to put the Talbot interferometer that employs the Talbot effect into practice, as set forth in, for instance, Tokkaisho 58-16216, Tokkai 2007-203063 (both are Japanese Patent Application Laid-Open Publications) and WO 2004/058070 Pamphlet (International Publication). The Talbot effect is defined as such a phenomenon that, when coherent light penetrate through the first grating in which plural slits are formed at constant intervals, a grating image thereof is focused at a constant period in the light traveling direction. This grating image is called a self-image. In the Talbot interferometer, the second grating is disposed at the focal position of the self-image, so as to measure interference fringes (Moire fringes) generated by slightly shifting the second grating. Since a pattern of the Moire fringes is deformed by placing an object in front of the second grating, when the Talbot interferometer is employed for the X-ray image capturing operation, it is possible to acquire a reproduced image of the subject by irradiating coherent X-rays onto the subject placed in front of the first grating and by applying an arithmetic calculation processing to the acquired Moire image.

Considering the practical realization, it has been expected to put the Talbot-Lau interferometer, in which a multi slit element is disposed between an X-ray source and the first grating so as to increase the amount of X-rays to be irradiated onto the subject, into practice.

For instance, when the Talbot-Lau interferometer is employed for capturing an X-ray image to be used for diagnosing the rheumatic disease, it is preferable that the X-ray image capturing apparatus is configured as a vertical type, in which the X-rays are irradiated onto the subject in a direction of gravitational force from the ceiling to the floor. If vertical type, it becomes easy to capture an image of the hand or the like at which the rheumatic is liable to be developed, and it becomes possible to reduce the installation area on which the X-ray image capturing apparatus is to be installed.

According to the conventional Talbot-Lau interferometer, when a reconfigured image is created by employing the stripe scanning method, a plurality of Moire images, which are different from each other in phase of strips corresponding to the relative positions of the first grating and the second grating (hereinafter, referred to as the Moire images at constant periods), is captured by shifting the first grating and the second grating (relatively shifting both the gratings). In the case that the X-ray image capturing apparatus is configured as a vertical type in order to reduce the installation area on which the concerned apparatus is to be installed, the first grating and/or the second grating are/is disposed at such a position that is nearer to the floor than that of a driving system for moving them, namely, disposed in the vicinity of the feet of the patient. In this structure, there would arise such a fear that the patient would contact the housing of the driving system, and as a result, unexpected impacts or vibrations are incurred to the gratings. Further, when the patient rides on the wheelchair, the space around the feet of the patient becomes narrower than ever, the abovementioned vibration problem has been liable to occur. Since it would be concerned that the high precision shift control cannot be achieved under such the vibration occurring environment, it is necessary for the operator to wait the X-ray image capturing operation until the influence of the vibration is eliminated. Further, it should be necessary to guide the patient to an appropriate position so as not to contact the housing of the driving system located in the vicinity of the patient's feet, and as a result, the direction of inserting the patient's hands or the like into the subject placing plate is limited. Alternatively, it should be necessary to request the patient of relatively advanced age to stretch the patient's hands or the like from the position being apart from the subject placing plate. As a result, since a certain stress is imposed to the patient concerned, such the practice is not preferable.

Since such the inconveniences as abovementioned have been predicted so far, it has been considered that it is difficult to put the X-ray image capturing apparatus, which employs the Talbot-Lau interferometer configured as the vertical type, into practice.

SUMMARY OF THE INVENTION

To overcome the abovementioned drawbacks in conventional X-ray image capturing apparatuses, it is one of objects of the present invention to provide a novel X-ray image creation method and a novel X-ray image capturing apparatus, to each of which the Talbot-Lau interferometer is applied, and specifically, to provide a vertical-type X-ray image capturing apparatus.

Accordingly, at least one of the objects of the present invention can be attained by any one of the X-ray image capturing apparatuses, the X-ray imaging systems and the X-ray image creation method, described as follows.

(1) According to an X-ray image capturing apparatus reflecting an aspect of the present invention, the X-ray image capturing apparatus, comprises: an X-ray source to emit X-rays to be irradiated onto a subject; a multi slits element having a plurality of slits; a first grating; a second grating; a driving section to move the multi slits element; a subject placing plate to place the subject thereon; and an X-ray detector in which conversion elements to convert intensities of X-rays received thereby to electric signals are arranged in a two-dimensional pattern, so as to read the electric signals converted by the conversion elements as image signals; wherein the driving section moves the multi slits element relative to both the first grating and the second grating in a first direction orthogonal to a second direction of irradiating the X-rays, so that the X-ray detector repeats a processing for reading the electric signals converted from the intensities of X-rays received thereby, every time when the multi slits element moves at predetermined intervals, so as to acquire the image signals representing Moire images captured at the predetermined intervals.

(2) According to another aspect of the present invention, in the X-ray image capturing apparatus recited in item 1, the X-ray source, the multi slits element, the subject placing plate, the first grating, the second grating and the X-ray detector are aligned in an order same as above-indicated.

(3) According to still another aspect of the present invention, the X-ray image capturing apparatus, recited in item 2, further comprises: a first supporting section to support both the first grating and the second grating; wherein a positional relationship between the first grating and the second grating in the second direction of irradiating the X-rays is fixed.

(4) According to still another aspect of the present invention, in the X-ray image capturing apparatus recited in item 3, the first supporting section also supports at least one of the multi slits element, the X-ray detector and the subject placing plate, integrally with the first grating and the second grating; and positional relationships between said at least one of the multi slits element, the X-ray detector and the subject placing plate, and both the first grating and the second grating in the second direction of irradiating the X-rays, are fixed.

(5) According to still another aspect of the present invention, the X-ray image capturing apparatus, recited in any one of items 1-4, further comprises: a second supporting section to support the subject placing plate; wherein the second supporting section is physically separated from the first supporting section by which the multi slits element is supported.

(6) According to still another aspect of the present invention, in the X-ray image capturing apparatus recited in any one of items 1-5, the driving section repeats the operation for moving and stopping the multi slits element at the predetermined intervals, so that the X-ray detector repeats the processing for reading the electric signals converted from the intensities of X-rays received, every time when the multi slits element stops at the predetermined intervals.

(7) According to still another aspect of the present invention, in the X-ray image capturing apparatus recited in any one of items 1-5, the driving section continuously moves the multi slits element, so that the X-ray detector repeats the processing for reading the electric signals converted from the intensities of X-rays received, corresponding to the X-rays periodically emitted by the X-ray source at the predetermined intervals.

(8) According to an X-ray imaging system reflecting still another aspect of the present invention, the X-ray imaging system, comprises: an X-ray image capturing apparatus that is provided with: an X-ray source to emit X-rays to be irradiated onto a subject; a multi slits element having a plurality of slits; a first grating; a second grating; a driving section to move the multi slits element; a subject placing plate to place the subject thereon; and an X-ray detector in which conversion elements to convert intensities of X-rays received thereby to electric signals are arranged in a two-dimensional pattern, so as to read the electric signals converted by the conversion elements as image signals; wherein the driving section moves the multi slits element relative to both the first grating and the second grating in a first direction orthogonal to a second direction of irradiating the X-rays, so that the X-ray detector repeats a processing for reading the electric signals converted from the intensities of X-rays received thereby, every time when the multi slits element moves at predetermined intervals, so as to acquire the image signals representing Moire images captured at the predetermined intervals; and an image processing apparatus that receives the image signals representing the Moire images captured by the X-ray image capturing apparatus, and processes the image signals received, so as to create a restructured image of the subject.

(9) According to still another aspect of the present invention, in the X-ray imaging system recited in item 8, the X-ray source, the multi slits element, the subject placing plate, the first grating, the second grating and the X-ray detector are aligned in an order same as above-indicated.

(10) According to still another aspect of the present invention, in the X-ray imaging system recited in item 9, the X-ray image capturing apparatus is further provided with a first supporting section to support both the first grating and the second grating; and wherein a positional relationship between the first grating and the second grating in the second direction of irradiating the X-rays is fixed.

(11) According to still another aspect of the present invention, in the X-ray imaging system recited in item 10, the first supporting section also supports at least one of the multi slits element, the X-ray detector and the subject placing plate, integrally with the first grating and the second grating and positional relationships between said at least one of the multi slits element, the X-ray detector and the subject placing plate, and both the first grating and the second grating in the second direction of irradiating the X-rays, are fixed.

(12) According to still another aspect of the present invention, in the X-ray imaging system recited in any one of items 8-11, the X-ray image capturing apparatus is further provided with a second supporting section to support the subject placing plate; and the second supporting section is physically separated from the first supporting section by which the multi slits element is supported.

(13) According to still another aspect of the present invention, in the X-ray imaging system recited in any one of items 8-12, the driving section repeats the operation for moving and stopping the multi slits element at the predetermined intervals, so that the X-ray detector repeats the processing for reading the electric signals converted from the intensities of X-rays received, every time when the multi slits element stops at the predetermined intervals.

(14) According to still another aspect of the present invention, in the X-ray imaging system recited in any one of items 8-12, the driving section continuously moves the multi slits element, so that the X-ray detector repeats the processing for reading the electric signals converted from the intensities of X-rays received, corresponding to the X-rays periodically emitted by the X-ray source at the predetermined intervals.

(15) According to an X-ray image creation method reflecting still another aspect of the present invention, the X-ray image creation method that is to be employed in an X-ray image capturing apparatus, which is provided with: an X-ray source to emit X-rays to be irradiated onto a subject; a multi slits element having a plurality of slits; a first grating a second grating a subject placing plate to place the subject thereon; and an X-ray detector in which conversion elements to convert intensities of X-rays received thereby to electric signals are arranged in a two-dimensional pattern, so as to read the electric signals converted by the conversion elements as image signals, the X-ray image creation method comprises: moving the multi slits element relative to both the first grating and the second grating in a first direction orthogonal to a second direction of irradiating the X-rays; making the X-ray detector repeat a processing for reading the electric signals converted from the intensities of X-rays received thereby, every time when the multi slits element moves at predetermined intervals, so as to acquire the image signals representing a plurality of Moire images captured at the predetermined intervals; and creating a restructured image of the subject based on the image signals representing the plurality of Moire images concerned.

(16) According to yet another aspect of the present invention, in the X-ray image creation method recited in item 15, the X-ray source, the multi slits element, the subject placing plate, the first grating, the second grating and the X-ray detector are aligned in an order same as above-indicated.

BRIEF DESCRIPTION OF THE DRAWINGS

Embodiments will now be described, by way of example only, with reference to the accompanying drawings which are meant to be exemplary, not limiting and wherein like elements are numbered alike in several Figures, in which:

FIG. 10c shows a schematic diagram indicating a reconstructed image that is restructured from Moire images respectively captured in five steps shown in FIG. 10a;

FIG. 11c shows a schematic diagram indicating a restructured image that is restructured from Moire images respectively captured in five steps shown in FIG. 11a;

DETAILED DESCRIPTION OF THE PREFERRED EMBODIMENT

Figure 1:
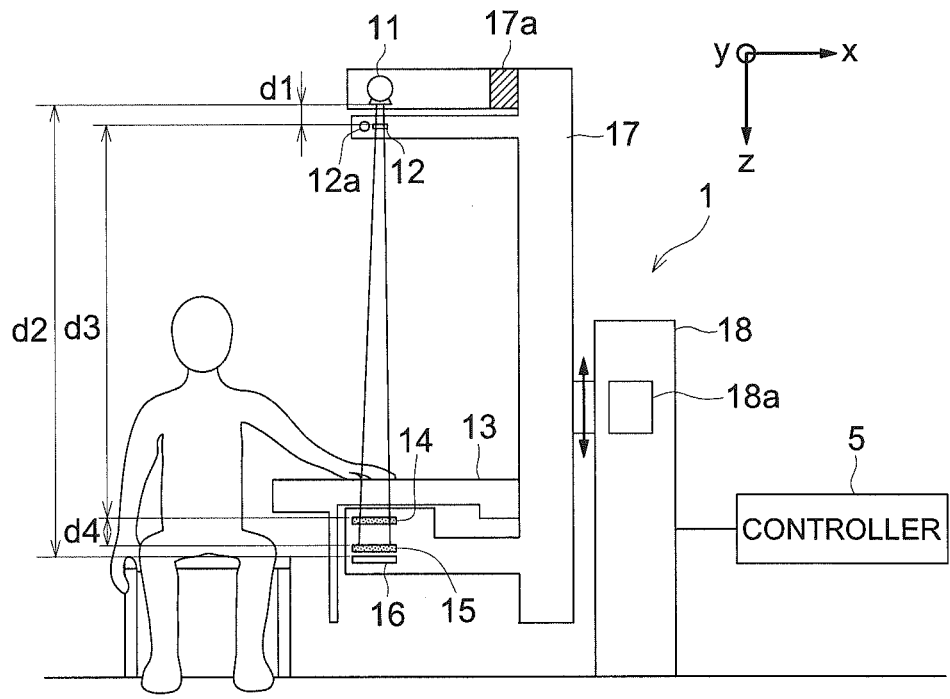
FIG. 1 shows a schematic diagram indicating a side view of an X-ray imaging system embodied in the present invention.

As a result of the intensive considerations made by the present inventors, it has been revealed by the present inventors that, instead of sticking the configuration of the Talbot-Lau interferometer on the conventional concept for the functions of the Talbot-Lau interferometer that a plurality of Moire images is created by shifting the first grating relative to the second grating or by shifting the second grating relative to the first grating, and the amount of X-rays to be irradiated onto the subject is increased by the multi slits, it is also possible to acquire the Moire images, which are equivalent to those acquired by employing the conventional Talbot-Lau interferometer, by employing such a configuration that the positions of the first grating and the second grating are fixed (no relative movement between them), and the multi slits is made to move relative to the first grating and the second grating concerned. According to the novel configuration as abovementioned, it becomes possible to solve the problems inherent to the conventional Talbot-Lau interferometer, specifically the problem to be predicted when the elements, included in the Talbot-Lau interferometer, are arranged (configured) in the vertical direction. As a result, it becomes possible to put the vertical-type X-ray image capturing apparatus, employing the Talbot-Lau interferometer, into practice.

Now, referring to the drawings, the embodiment of the present invention will be detailed in the following.

FIG. 1 shows a schematic diagram indicating an X-ray imaging system embodied in the present invention. The X-ray imaging system is provided with an X-ray image capturing apparatus 1 and a controller 5. The X-ray image capturing apparatus 1 serves as a Talbot-Lau interferometer that performs an X-ray image capturing operation, while the controller 5 employs Moire images acquired by the X-ray image capturing operation so as to creates a restructured image of the subject.

As shown in FIG. 1, the X-ray image capturing apparatus 1 is provided with an X-ray source 11, a multi slits element 12, a subject placing plate 13, a first grating 14, a second grating 15 and an X-ray detector 16, which are arranged in the above-indicated order in a z-direction serving as a direction of gravitational force. Further, hereinafter, a distance between a focal point of the X-ray source 11 and the multi slits element 12, another distance between the focal point of the X-ray source 11 and the X-ray detector 16, still another distance between the multi slits element 12 and the first grating 14, and yet another distance between the first grating 14 and the second grating 15 are represented by a distance "d1", a distance "d2", a distance "d3" and a distance "d4", respectively.

It is preferable to establish the distance "d1" at a value in a range of 5-500 mm, and more preferably in a range of 5-300 mm.

Since a height of an image capturing room is generally set at about 3 meter or smaller, it is preferable to establish the distance "d2" at a value equal to or smaller than 3000 mm Among other things, it is preferable to establish the distance "d4" at a value in a range of 400-5000 mm, and more preferably in a range of 500-2000 mm.

Further, it is preferable to establish the distance between the focal point of the X-ray source 11 and the first grating 14 "d1+d3" at a value in a range of 30-5000 mm, and more preferably in a range of 400-1800 mm.

Still further, it is preferable to establish the distance between the focal point of the X-ray source 11 and the second grating 15 "d1+d3+d4" at a value in a range of 400-5000 mm, and more preferably in a range of 500-2000 mm.

It is applicable that each of the distances is established by calculating an optimum distance, which makes the grating images (self-images), projected onto the second grating 15 by the first grating 14, overlap with each other, from the wavelength of the X-ray to be irradiated from the X-ray source 11.

The X-ray source 11, the multi slits element 12, the subject placing plate 13, the first grating 14, the second grating 15 and the X-ray detector 16 are integrally supported by a supporting member 17 serving as a common support member, so as to fix the positional relationship between them in the z-direction. The supporting member 17 is formed in a alphabetical "C" letter shape, and is fixed to a driving section 18a protruded from a main body section 18, so as to make it possible to move the supporting member 17 in the z-direction.

The X-ray source 11 is fixed onto the supporting member 17, while placing a buffer member 17a between them. Any kind of material can be employed as the buffer member 17a as far as the material can absorb impacts and vibrations, and, for instance, an elastomer or the like can be cited as the material concerned. Since the X-ray source 11 also generates considerable amount of heats associating with the X-ray irradiating action, it is preferable that the supporting member 17 to be attached to the X-ray source 11 has a heat insulation property in addition to the above.

The X-ray source 11 is provided with an X-ray tube, and makes the X-ray tube generate X-rays so as to irradiate the X-rays in the direction of gravitational force (z-direction). For instance, the Coolidge X-ray tube or the rotation anode X-ray tube, which has been widely employed in the medical field, can be employed as the X-ray tube abovementioned. Further, tungsten or molybdenum can be employed as the anode material.

It is preferable that a diameter of the X-ray focal point is set at a value in a range of 0.03-3 mm, and more preferable in a range of 0.1-1 mm.

Figure 2:
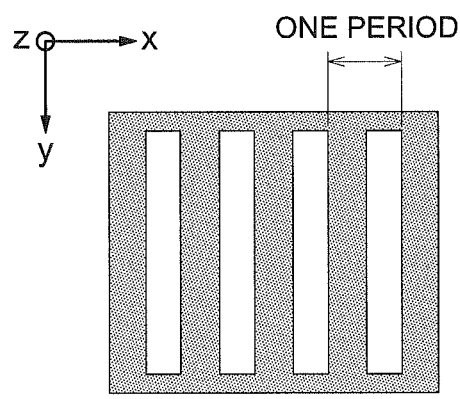
FIG. 2 shows a schematic diagram indicating a plane view of a multi slits element.

The multi slits element 12 serves as a diffraction grating in which a plurality of slits is arranged at predetermined intervals in an x-direction as shown in FIG. 2. The multi slits element 12 is formed by coating a material having a property for strongly shielding the X-rays, namely, the X-ray absorption rate of which is relatively high, such as a tungsten, a lead, a gold or the like, onto a substrate, the X-ray absorption rate of which is relatively low, such as a silicon, a glass or the like. For instance, according to the photolithography method, the resist layer is masked by the slit pattern, and the UV (Ultra Violet) light is irradiated thereon so as to transfer the slit pattern onto the resist layer. Further, the slits structure, being same as that of the slit pattern concerned, is acquired by applying the exposure processing, and then, a metal material is embedded into the gaps between the slits of the concerned slits structure by employing the electroforming method.

The slit period of the multi slits element 12 is set at a value in a range of 1-60 μm. The slit period is defined as a distance between two adjacent slits, as shown in FIG. 2. The width of the slit (length in the x-direction) is preferably set at a value in a range of 1%-60% of the slit period, and more preferably, in a range of 10%-40% of the slit period. The height of the slit (length in the z-direction) is set at a value in a range of 1-500 μm, and preferably, in a range of 1-150 μm.

When a slit period "$w_0$" (μm) represents a value of the slit period of the multi slits element 12, and another slit period "$w_1$" (μm) represents another value of the slit period of the first grating 14, the slit period "$w_0$" can be found by employing the Equation indicated as follow.

$$w_0 = w_1 \times (d3+d4)/d4$$

By determining the slit period "$w_0$" so as to fulfill the Equation concerned, it is possible to make the self-images, formed by the X-rays passing through each of the slits of the multi slits element 12 and the first grating 14, overlap with each other on the second grating 15, namely, to make them enter into an in-focus state.

As shown in FIG. 1, a driving section 12a, to move the multi slits element 12 in the x-direction (slits arrangement direction) orthogonal to the z-direction, is disposed at a position being adjacent to the multi slits element 12. It is possible to employ a single unit or an assembly (combination) of a driving motor and a driving mechanism (driving force transmission mechanism) having a relatively large reduction ratio, such as a worm reducer, etc., as the driving section 12a.

As well as the multi slits element 12, the first grating 14 serves as a diffraction grating in which a plurality of slits is formed in the x-direction. It is applicable that the first grating 14 can be formed either by employing the photolithography method using the UV (Ultra Violet) light as well as the multi slits element 12, or by employing the ICP (Inductive Coupled Plasma) method to apply the deep grooving treatment to a silicon substrate by using a fine wire (needle) so as to form a lattice structure only for the silicon substrate. The slit period of the first grating 14 is set at a value in a range of 1-20 μm. The width of the slit is set at a value in a range of 20%-70% of the slit period, and preferably, in a range of 35%-60% of the slit period. The height of the slit is set at a value in a range of 1-100 μm.

When a phase type grating is employed as the first grating 14, the height of the slit (length in the z-direction) is set at such a height that makes a phase difference, caused by the two kinds of materials, which form the slit period, namely, the X-ray penetration (transparent) section and the X-ray shielding section, equal to a value in a range of $\pi/8$-$15\times\pi/8$, and preferable in a range of $\pi/4$-$3\times\pi/4$. On the other hand, when an absorption type grating is employed as the first grating 14, the height of the slit is set at such a height that makes the X-ray shielding section sufficiently absorb the X-ray.

When the first grating 14 serves as the phase type grating, it is necessary for the distance "d4" between the first grating 14 and the second grating 15 to substantially fulfill the condition represented by the Equation indicated as follow.

$$d4 = (m + (1/2)) \times w_1^2 / \lambda$$

where "m" is an integer, and "λ" is a wavelength of the X-ray concerned.

As well as the multi slits element 12, the second grating 15 serves as a diffraction grating in which a plurality of slits is formed in the x-direction. The second grating 15 can be also formed by employing the photolithography method. The slit period of the second grating 15 is set at a value in a range of 1-20 μm. The width of the slit is set at a value in a range of 30%-70% of the slit period, and preferably, in a range of 35%-60% of the slit period. The height of the slit is set at a value in a range of 1-100 μm.

In the present embodiment, the first grating 14 and the second grating 15 are arranged in such a manner that the grating surface of each of them is perpendicular to the z-direction (parallel in the x-y plane), while, the slit arrangement direction of the first grating and the slit arrangement direction of the second grating are inclined to each other at a predetermined angle within the x-y plane. However, it is also applicable that both are arranged in parallel.

For instance, it is possible to configure the multi slits element 12, the first grating 14 and the second grating 15, above-mentioned, in such a manner as described in the following.

Diameter of a focal point of the X-ray tube provided in the X-ray source 11: 300 μm, Tube voltage: 40 kVp, Additional filter: aluminum 16 mm Distance "d1" from the focal point of the X-ray source 11 to the multi slits element 12: 240 mm Distance "d3" from the multi slits element 12 to the first grating 14: 1110 mm Distance "d3+d4" from the multi slits element 12 to the second grating 15: 1370 mm Distance "d1" from the focal point of the X-ray source 21 to the multi slits element 12: 34 mm Size of the first grating 14: 50 square-mm, Slit period: 4.3 μm Size of the second grating 15: 50 square-mm, Slit period: 5.8 μm The X-ray detector 16, in which a plurality of converting elements to generate electric signals, corresponding to amounts of the irradiated X-rays, are two-dimensionally arranged, reads the electric signals, generated by the plurality of converting elements, as image signals.

The size of each of pixels included in the X-ray detector 16 is preferably set at a value in a range of 10-300 μm, and more preferably, in a range of 50-200 μm.

It is preferable that the position of the X-ray detector 16 is fixed onto the supporting member 17 in such a manner that the X-ray detector 16 contacts the second grating 15. This is because, the larger the distance between the second grating 15 and the X-ray detector 16 becomes, the more the Moire image acquired by the X-ray detector 16 is blurred.

An FPD (Flat Panel Detector) can be employed as the X-ray detector 16. Although there have existed two different types of FPDs, including the indirect conversion type FPD, in which the photo-electric conversion elements convert intensities of received X-rays to electric signals through the scintillator, and the direct conversion type FPD, in which the intensities of received X-rays are directly converted to electric signals, any one of them is applicable in the present embodiment.

In the indirect conversion type FPD, under the scintillator plate made of CsI, $Gd_2O_3$, $Gd_2O_3S$, etc., the photo-electric conversion elements associating with the TFTs (Thin Film Transistors) are arranged in a two-dimensional pattern, so as to constitute each of the pixels. When absorbing the X-rays currently entered into the X-ray detector 16, the scintillator plate emits light. In response to the emitted light, each of the photo-electric conversion elements generates and stores a corresponding amount of electric charge therein, and successively, the stored electric charges are read out as the electric signals.

On the other hand, the direct conversion type FPD is structured in such a manner that an amorphous selenium film, having a film thickness in a range of 100-1000 μm, is formed on the glass substrate by employing the amorphous-selenium thermal deposition processing, and then, the amorphous selenium film and the electrodes are vapor-deposited onto the TFT array arranged in a two-dimensional pattern. When the amorphous selenium film absorbs the X-ray, a carrier is liberated into the concerned substance in the form of a pair of an electron and a hole, and then, the TFT reads out (detects) the voltage signal between the electrodes.

In this connection, it is also applicable that a kind of image capturing device, such as a CCD (Charge Coupled Device), an X-ray camera, etc., is employed as the X-ray detector 16.

Now, the consecutive processing to be conducted at the time of implementing the X-ray image capturing operation will be detailed in the following.

Initially, a resetting operation is applied to the FPD, so as to remove the unnecessary residual electric charges still remaining within the FPD after the previous image capturing operation has been completed. After that, the electric charge storing action is performed at the timing when the X-ray irradiating operation is commenced, and the stored electric charges are read out as the image signals at the timing when the X-ray irradiating operation is completed. In this connection, it is applicable that, just after the resetting operation is completed, and/or after the image signals have been read out, the dark voltage reading operation for detecting the electric charges, currently stored within the FPD, is implemented, so as to output the voltage values, derived by subtracting the concerned dark voltage, serving as the correction value, from the voltage values representing the electric charges stored after the X-rays have been irradiated, as the image signals. According to the abovementioned operation, it becomes possible to apply the offset correction processing to the image signals.

Figure 3:
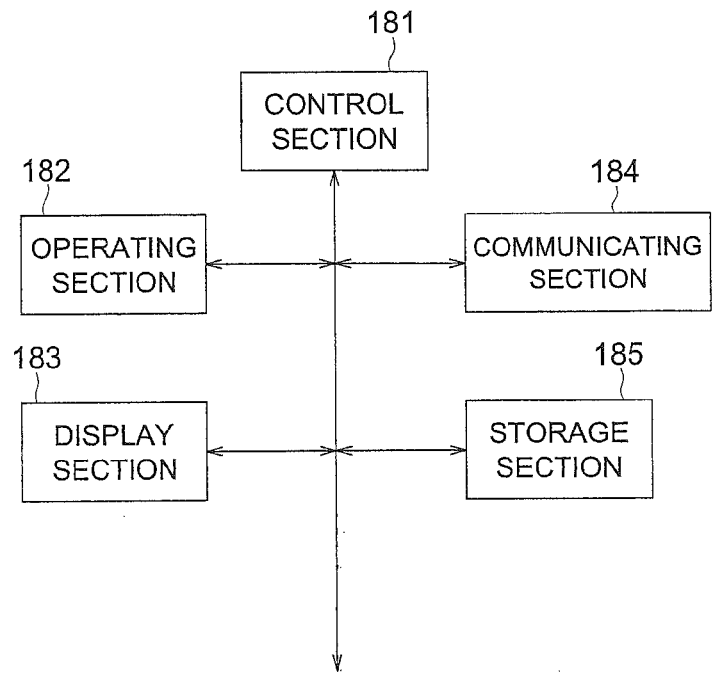
FIG. 3 shows a block diagram indicating a functional configuration of a main body section.

As shown in FIG. 3, the main body section 18 is constituted by a control section 181, an operating section 182, a display section 183, a communicating section 184 and a storage section 185.

The control section 181 is constituted by a CPU (Central Processing Unit), a RAM (Random Access Memory), etc., to execute various kinds of programs stored in the storage section 185, so as to implement various kinds of processing. For instance, the control section 181 controls the timing for irradiating the X-rays emitted from the X-ray source 11 onto the subject, the other timing for making the X-ray detector 16 read the image signals, etc.

Other than an X-ray exposure switch and a group of keys to be used for various kinds of inputting operations, the operating section 182 is provided with a touch panel that is integrally configured with a display screen of the display section 183, so as to output operational signals, created corresponding to the operations therefrom, to the control section 181.

Under the display controlling operations conducted by the control section 181, the display section 183 displays various kinds of operating screens and operating statuses of the X-ray image capturing apparatus 1 on the display screen.

The communicating section 184 is provided with a communication interface, in order to communicate with the controller 5 coupled to the network. For instance, the communicating section 184 transmits Moire image data, which has been read by the X-ray detector 16 and stored in the storage section 185, to the controller 5.

The storage section 185 stores the programs to be executed by the control section 181, and the data necessary for executing the programs, therein. Further, the storage section 185 also stores the Moire image data acquired by the X-ray detector 16, therein.

According to the operations inputted by the operator, the controller 5 controls the image capturing operations to be implemented by the X-ray image capturing apparatus 1, so as to create a restructured image of the subject by employing the Moire images acquired by the X-ray image capturing apparatus 1. Although an embodiment that employs the controller 5 will be exemplified as an image processing apparatus that creates the restructured image of the subject, in the following, it is also applicable that the system is so constituted that an exclusive image processing apparatus for applying various kinds of processing to the X-ray image data is coupled to the X-ray image capturing apparatus 1, so that the exclusive image processing apparatus implements the operations for creating the restructured image concerned.

The X-ray image capturing method that employs the Talbot-Lau interferometer included in the X-ray image capturing apparatus 1 abovementioned will be detailed in the following.

Figure 4:
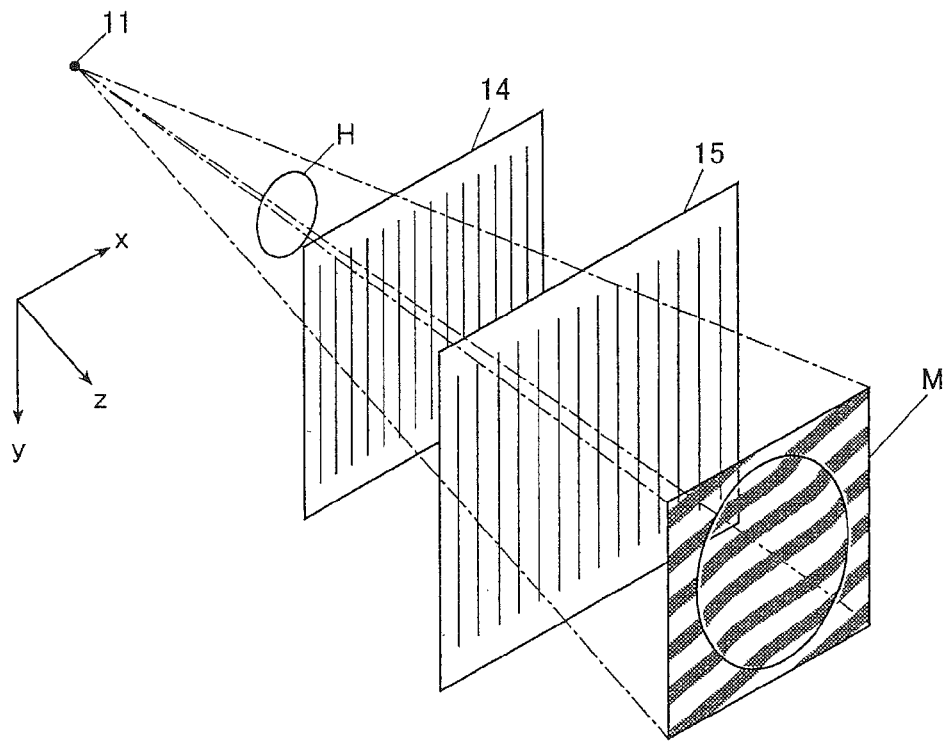
FIG. 4 shows a schematic diagram indicating an explanatory perspective view for explaining a principle of the Talbot interferometer.

As shown in FIG. 4, when the X-rays emitted from the X-ray source 11 penetrate through the first grating 14, the penetrated X-rays project focused images at constant intervals in the z-direction. This image is defined as a self-image, and the phenomenon for forming the self-image is defined as a Talbot effect. Since the second grating 15 is disposed at such a position at which the self-image is focused, and the grating direction of the second grating 15 is made to be slightly inclined with respect to the position parallel to that of the first grating 14, a Moire image M formed by the X-rays penetrated through the second grating 15 can be acquired. When a subject H exists at a position between the X-ray source 11 and the first grating 14, since phases of the X-rays are shifted by the subject H, the interference fringes on the Moire image are deformed (distorted) at the border of the periphery edge of the subject H. Accordingly, it is possible to detect the deformations (distortions) of the interference fringes by processing the Moire image M so as to visualize (reproduce) the subject image as a visible image. The abovementioned process is the principle of the Talbot interferometer.

In the X-ray image capturing apparatus 1, the multi slits element 12 is disposed at a position located between the X-ray source 11 and the first grating 14, and near to the X-ray source 11, in order to implement the X-ray image capturing operation employing the Talbot-Lau interferometer. Although the Talbot interferometer is to be operated on the premise that the X-ray source 11 is configured as an ideal point X-ray source, in reality, since the diameter of the focal point, formed by the X-ray source 11 to be employed, is expanded to some extent, the X-ray source 11 serving as a single point source is converted to multi X-ray sources by the multi slits element 12, as if the X-rays were irradiated from plural point X-ray sources aligned in a serial row. This is defined as the X-ray image capturing method employing the Talbot-Lau interferometer, and it is possible for the Talbot-Lau interferometer to achieve the Talbot effect being same as that acquired by the Talbot interferometer, even when the focal point is expanded to some extent.

In the conventional Talbot-Lau interferometer, the multi slits element 12 has been employed for the purpose of converting the single X-ray source to the plural point X-ray sources as abovementioned and the purpose of increasing an amount of X-rays to be irradiated, and the first grating 14 and the second grating 15 have been made to shift relative to each other in order to obtain the Moire image by employing the stripe scanning method. However, in the embodiment of the present invention, instead of shifting the first grating 14 and the second grating 15 relative to each other, the multi slits element 12 is made to shift relative to the first grating 14 and the second grating 15, while keeping the positions of the first grating 14 and the second grating 15 at fixed positions, respectively, so as to obtain a plurality of Moire images located at constant intervals.

FIG. 1 shows a flowchart indicating a flow of the X-ray image capturing operation to be implemented by the X-ray image capturing apparatus 1.

The X-ray image capturing method employing the Talbot-Lau interferometer abovementioned is employed for implementing the X-ray image capturing operation, while the stripe scanning method is employed for restructuring the subject image. In the X-ray image capturing apparatus 1, the multi slits element 12 is shifted step by step for plural times at constant intervals, in order to implement the X-ray image capturing operation for every step, so as to acquire the Moire image of each step.

It is preferable that a number of the steps is set at a value in a range of 2-20, and more preferable, in a range of 3-10. From such the viewpoint that a restructured image having a high visibility should be acquired within a short time interval, it is preferable that the number of the steps is set at 5 steps (Reference Document 1: K. Hibino, B. F. Oreb and D. I. Farrant, "Phase shifting for nonsinusoidal wave forms with phase-shift errors", J. Opt. Soc. Am. A, Vol. 12, 761-768 (1995), Reference Document 2: A Momose, W. Yashiro, Y. Takeda, Y. Suzuki and T. Hattori, "Phase Tomography by X-ray Talbot Interferometry for biological imaging", Jpn. J. Appl. Phys., Vol. 45,5254-5262 (2006)).

Figure 5:
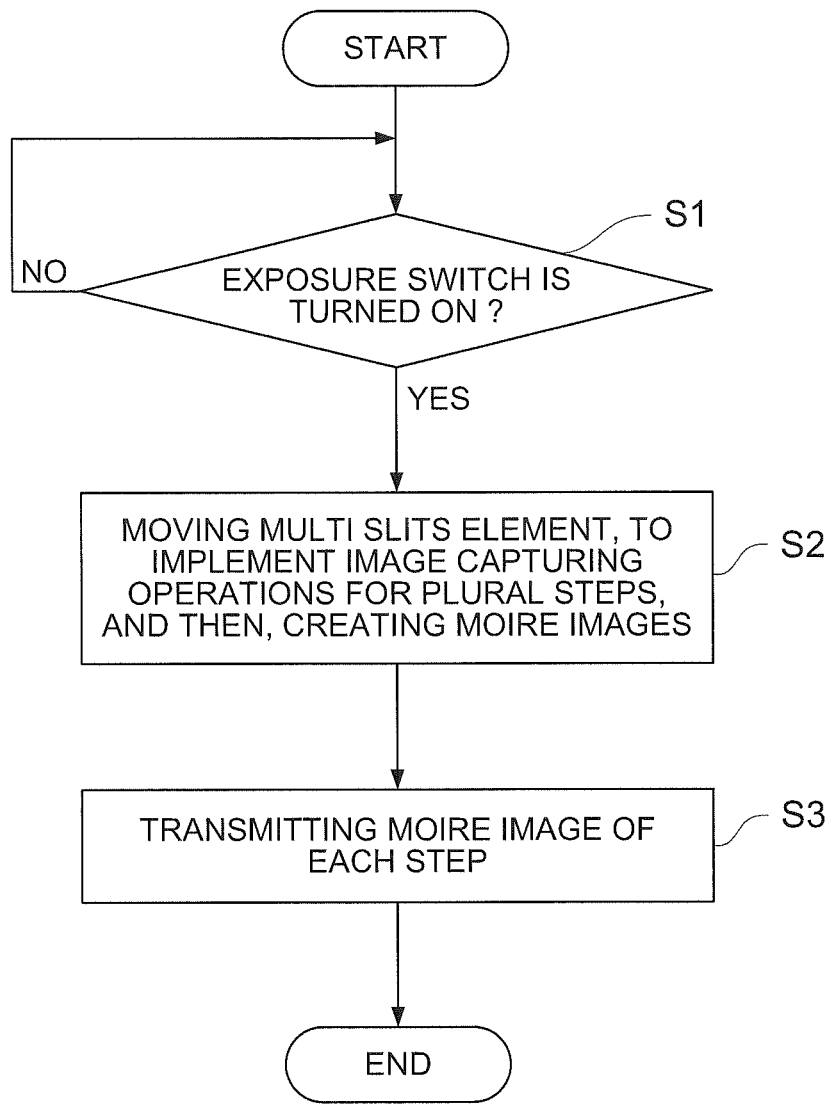
FIG. 5 shows a flowchart indicating processing to be conducted by an X-ray image capturing apparatus at the time of an X-ray image capturing operation.

As indicated in the flowchart shown in FIG. 5, when the operator turns ON the exposure switch (Step 51; Yes), the driving section 12a moves the multi slits element 12 so as to implement the image capturing operations for a plurality of steps, and then, the Moire images are created (Step S2).

At first, the X-ray irradiating operation to be conducted by the X-ray source 11 is commenced in the state that the multi slits element 12 is stopped at the initial position. Successively, in the X-ray detector 16, after the operation for resetting the residual electric charges has been completed, newly induced electric charges are stored in synchronization with the X-ray irradiation timing, and then, the stored electric charges are read out as the image signals in synchronization with the X-ray irradiation stoppage timing. The abovementioned process is equivalent to one step of the image capturing operation. Still successively, at the time when the one step of the image capturing operation has been completed, the operation for moving the multi slits element 12 is commenced, and then, moving a predetermined amount, the multi slits element 12 is stopped at the next position, so that the next step of the image capturing operation is implemented at the next position. As abovementioned, the sequential operations for moving and stopping the multi slits element 12 are repeated predetermined times that is equivalent to the predetermined number of the steps, so that the sequential operations for irradiating the X-rays and reading out the image signals are implemented at every time when the multi slits element 12 is stopped. The readout image signals are outputted to the main body section 18 as the Moire image data.

For instance, it is assumed that the slit period of the multi slits element 12 is set at 22.8 μm, and the image capturing operations of 5 steps are completed within 10 seconds. On this condition, the image capturing operation is implemented at every time when the multi slits element 12 moves 4.56 μm that is equivalent to ⅕ of the slit period thereof Speaking on the image capturing time domain, the image capturing operations are implemented at the times when 2, 4, 6 and 10 seconds have elapsed after the exposure switch was turned ON, respectively.

In such a conventional case that the second grating 15 (or the first grating 14) is made to move, the slit period of the second grating 15 becomes relatively small and the moving amount for each step also becomes small. However, the slit period of multi slits element 12 is relatively large and the moving amount for each step also is large. For instance, the moving amount of the second grating 15, having the slit period of 5.3 μm, is 1.06 μm, while the moving amount of the multi slits element 12, having the slit period of 22.8 μm, is 4.56 μm, which is four times of that of the second grating 15. In the case that the same driving transmission mechanism (including the driving source and the reduction transmission system) is employed for implementing the image capturing operations while repeating the sequential operations for activating and deactivating the driving section 12a every time when implementing the image capturing operation for each step, the proportion of the moving amount error, caused by influences of the backlashes of the driving section 12a or the like, generated at the time of the activation and deactivation thereof, versus, the actual moving amount, corresponding to the controlling amount (number of driving pulses) of the pulse motor for moving use (serving as the driving source), becomes relatively small in such the method, in which the multi slits element 12 is made to move, as achieved in the embodiment of the present invention. As detailed later, this results in an easiness of acquiring the Moire images and implies that a restructured image, having a high definition quality, can be obtained even if the activating and the deactivating operations are repeated. In other words, when the X-ray images acquired by the conventional method sufficiently comply with the medical diagnosis, the abovementioned fact indicates that it becomes possible to alleviate the demands for the accuracy of the whole driving transmission mechanism including the motor (the driving source), resulting in a cost reduction of the parts to be employed for the driving transmission mechanism.

Returning to the flowchart shown in FIG. 5, when the image capturing operation of each step is completed, the Moire image data, acquired in each step, is transmitted from 18 to the controller 5 (Step S3). It is applicable that a single set of Moire image data, representing one sheet of image, is transmitted every time when the image capturing operation has been completed, or all sets of Moire image data are transmitted at a time after all of the image capturing operations in all steps has been completed, and all sets of the Moire image data have been acquired.

Figure 8:
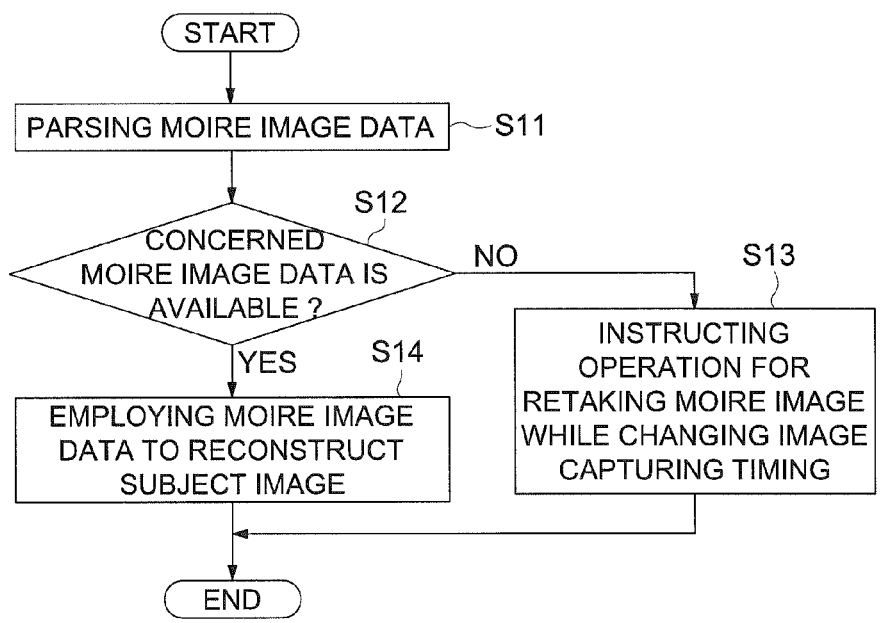
FIG. 8 shows a flowchart indicating a flow of processing operations to be conducted by a controller.

FIG. 8 shows a flowchart indicating a flow of processing operations to be conducted by the controller 5 after the controller 5 has received the Moire image data.

Figure 6:
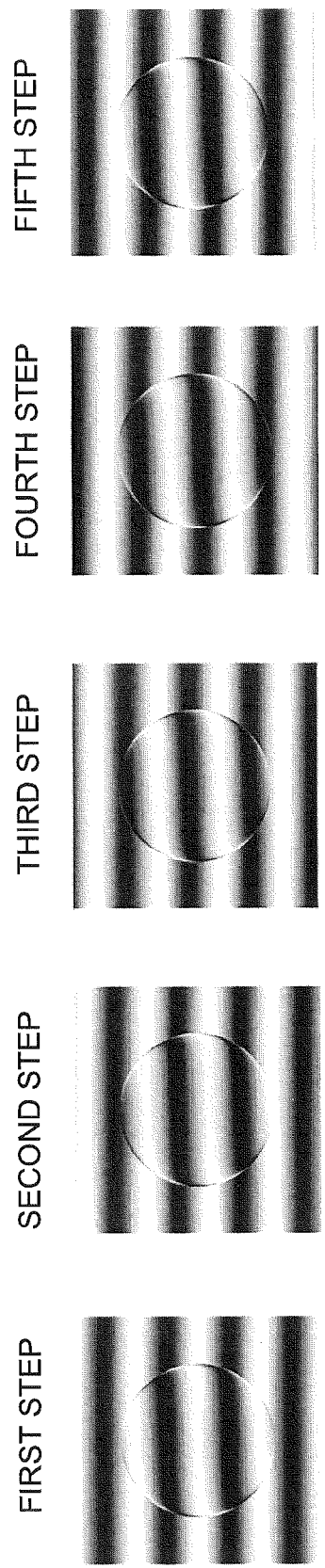
FIG. 6 shows a schematic diagram indicating Moire images acquired by implementing image capturing operations for five steps.
Figure 7:
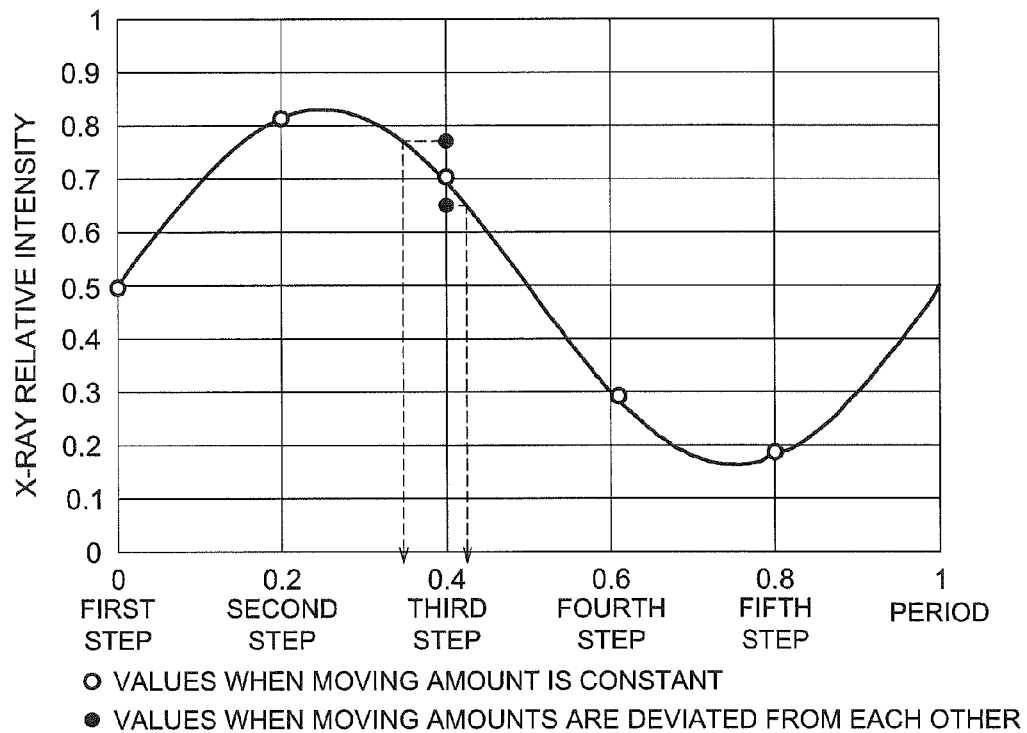
FIG. 7 shows a graph indicating an X-ray relative intensity curve of a pixel of interest included in a Moire image captured in each step.

As shown in FIG. 8, initially, the controller 5 parses the Moire image data (Step S11), so as to determine whether or not the concerned Moire image data can be employed for creating a restructured image (Step S12). When the operation for moving the multi slits element 12 by a constant moving amount could be achieved with an ideal moving accuracy, as shown in FIG. 6, five sheets of the Moire images, each of which corresponds to a single slit period of the multi slits element 12, can be obtained by repeating the image capturing operation five times corresponding to the five steps. Since the Moire image of each step is obtained as a result of implementing the stripe scanning operation for every constant period interval that is 0.2 period, the X-ray relative intensity acquired by normalizing the signal value thereof depicts a sine curve as shown in FIG. 7. Accordingly, the controller 5 finds the X-ray relative intensity by giving an attention to a certain pixel of the Moire image above-obtained in each of the five steps. If the X-ray relative intensities, each of which is found from each of the Moire images, form the sine curve shown in FIG. 7, since the Moire images captured at the constant period intervals have been obtained, it is possible to determine that the concerned Moire image data can be employed for creating the restructured image.

In this connection, the shape of the abovementioned sine curve depends on the aperture width of the multi slits, the period of phase grating and the grating gap distance of the phase grating, and, although, in the case of coherent light like radiant light, the curve is formed in a rectangular shape, since the X-rays serves as quasi-coherent light due to the multi slits effect, the curve is depicted as the sine curve.

When the Moire images, respectively obtained in the steps concerned, include such a Moire image that cannot ride on (cannot form) the sine curve, the controller 5 determines that the concerned Moire image data cannot be employed for creating the restructured image (Step S12; No), and transmit controlling information, representing an instruction for retaking the Moire image while changing the image capturing timing, to the X-ray image capturing apparatus 1 (Step S13). For instance, as shown in FIG. 7, if the Moire image has been erroneously obtained at 0.35 period that has shifted from the originally intended value of 0.4 period, it would be considered that the cause of the error is lies on the fact that the moving accuracy of the driving section 12a has been deteriorated (for instance, unexpected noise components overlap with the driving pluses for the pulse motor, etc.). Accordingly, it is applicable that the controller 5 instructs the X-ray image capturing apparatus 1 to advance the image capturing timing of the third step by 0.05 period, so as to retake the Moire image only at the third step. Alternatively, it is also applicable that the controller 5 instructs the X-ray image capturing apparatus 1 to retake all of the Moire images of the five steps, while advancing the image capturing timing only at the third step by 0.05 period. When the Moire images of all of the five steps are shifted from the sine curve by a predetermined amount, it is applicable that the controller 5 instructs the X-ray image capturing apparatus 1 to increase or decrease the number of driving pulses from the activation to the deactivation of the driving section 12a.

According to the controlling information concerned, the X-ray image capturing apparatus 1 adjusts the image capturing timing so as to again implement the processing flow of the X-ray image capturing operation, indicated by the flowchart shown in FIG. 5.

On the other hand, when determining that the concerned Moire image data can be employed for creating the restructured image (Step S12; Yes), the controller 5 applies necessary processing to the Moire image data, so as to reconstruct the image of the subject (Step S14). Concretely speaking, with respect to each of the pixels included in the five sheets of Moire images, the intensity change (change of the signal value) for every step is calculated, and successively, the differential phase is calculated from the intensity change concerned. If necessary, the phase connection (phase unwrap) processing is implemented to find the phase of all of the steps. Successively, the optical path difference (optical path difference caused by the refraction index difference) is calculated, and then, a restructured image, representing a shape of the subject, is created (referring to aforementioned Reference Documents (1) and (2)). Since the restructured image above-created is displayed on the controller 5, it is possible for the operator to confirm the restructured image concerned.

<Image Capturing Experiment>

The present inventors have implemented the image capturing experiment, described in the following, in order to verify the fact that, even when only the multi slits element 12 is made to move, instead of the first grating 14 or the second grating 15, it is possible to obtain the restructured image being substantially the same as that acquired by moving the first grating 14 and the second grating 15 relative to each other.

Figure 9:
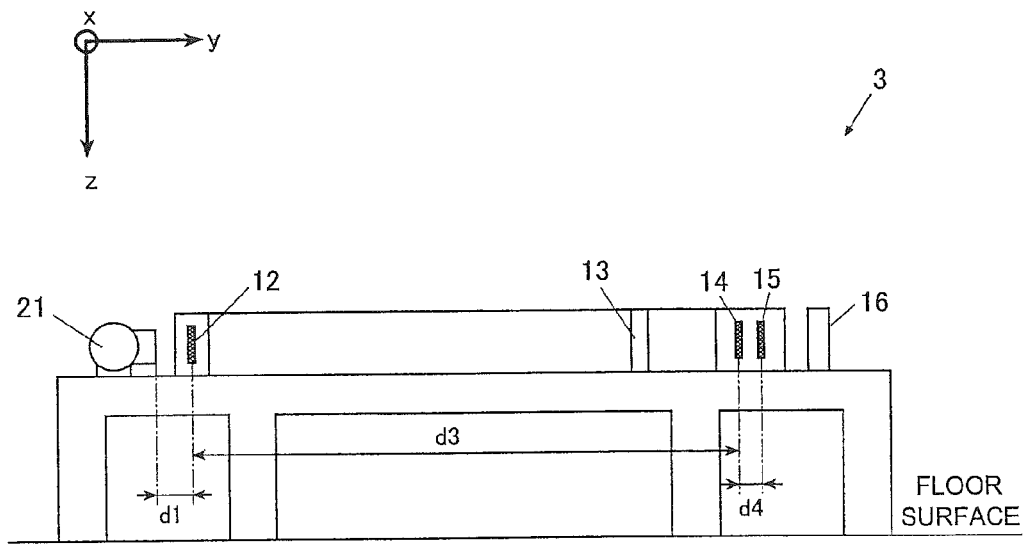
FIG. 9 shows a schematic diagram indicating a side view of a horizontal-type X-ray image capturing apparatus.

FIG. 9 shows a schematic diagram indicating the horizontal-type X-ray image capturing apparatus, which has been employed for the image capturing experiment concerned.

The present inventors assembled a horizontal-type X-ray image capturing apparatus 3 as a test model in which an X-ray source 21, the multi slits element 12, the subject placing plate 13, the first grating 14, the second grating 15 and the X-ray detector 16 are arranged in the horizontal direction (y-direction) in this order, so as to employ the concerned test model for the image capturing experiment. Further, the present inventors have employed such an X-ray tube that was reformed from a commercially available X-ray tube by replacing the molybdenum with the tungsten, as the X-ray source 21.

On the test model concerned, the first image capturing operations were performed by sifting the multi slits element 12 in the x-direction, so as to obtain the Moire images. Then, the restructured image was created on the basis of the above-obtained Moire images. Successively, the second image capturing operations were performed by sifting the second grating 15 in the x-direction, and the restructured image was created as well as the above.

The image capturing conditions employed in this experiment are indicated as follows. The same image capturing conditions have been applied to both the first image capturing operations and the second image capturing operations.

Figure 10A:
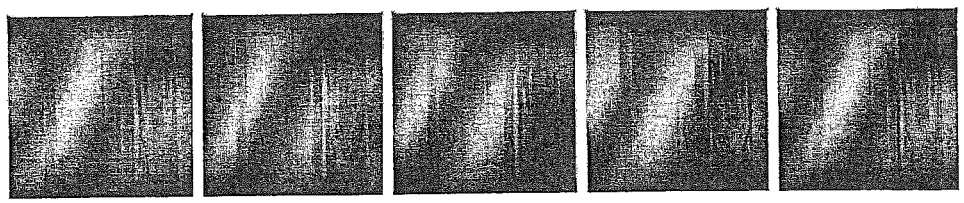
FIG. 10a shows a schematic diagram indicating Moire images, respectively corresponding to steps and captured by shifting a multi slits element, when a subject is placed.
Figure 10B:
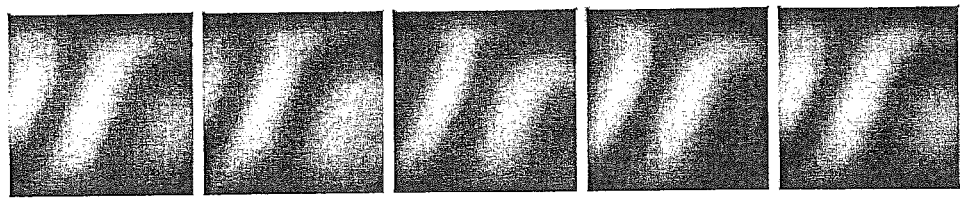
FIG. 10b shows a schematic diagram indicating Moire images, respectively corresponding to steps and captured by shifting a multi slits element, when no subject is placed.
Figure 10C:
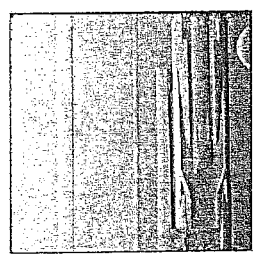

Diameter of a focal point of the X-ray tube: 300 µm, Tube voltage: 40 kVp, Additional filter: aluminum 16 mm, Central energy: 28 keV X-ray detector: Condor 486 (manufactured by Fairchild Imaging Co. Ltd.), Pixel size: 15 µm Distance "d1" from the focal point of the X-ray source 11 to the multi slits element 12: 34 mm Distance "d3" from the multi slits element 12 to the first grating 14: 1110 mm Distance "d3+d4" from the multi slits element 12 to the second grating 15: 1370 mm Size of the multi slits element 12: 5 square-mm, Slit period: 22.8 µm Size of the first grating 14: 50 square-mm, Slit period: 4.3 µm Size of the second grating 15: 50 square-mm, Slit period: 5.8 µm FIG. 10a through FIG. 10c show photographic schematic diagrams indicating images captured by shifting the multi slits element 12. FIG. 10a shows photographic schematic diagrams indicating images captured by shifting the multi slits element 12, when the subject is placed at subject placing plate 13. FIG. 10b shows photographic schematic diagrams indicating images captured by shifting the multi slits element 12, when no subject is placed at subject placing plate 13. FIG. 10c shows a photographic schematic diagram indicating an image that is restructured from the Moire images respectively captured in the five steps shown in FIG. 10a.

Figure 11A:
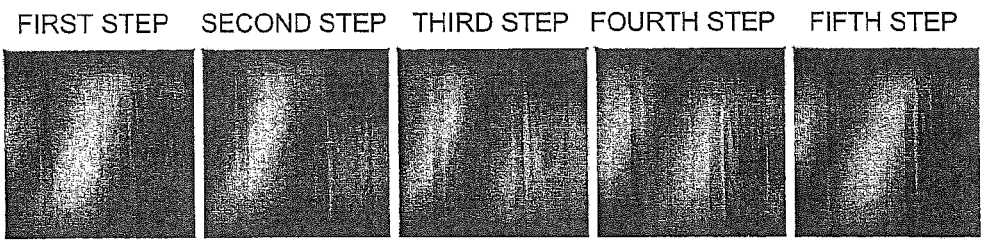
FIG. 11a shows a schematic diagram indicating Moire images, respectively corresponding to steps and captured by shifting a second grating, when a subject is placed.
Figure 11B:
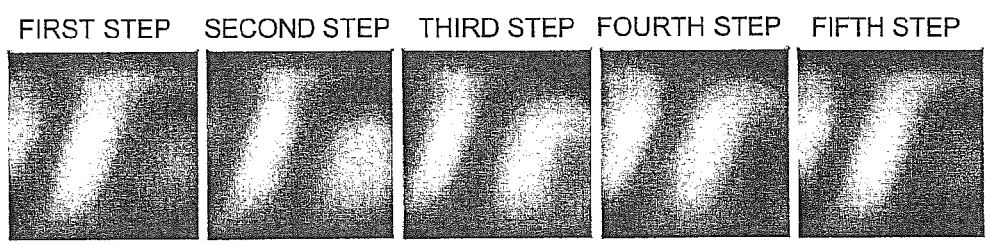
FIG. 11b shows a schematic diagram indicating Moire images, respectively corresponding to steps and captured by shifting a second grating, when no subject is placed.
Figure 11C:
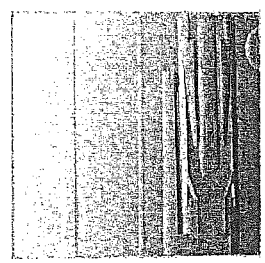

On the other hand, FIG. 11a through FIG. 11c show photographic schematic diagrams indicating images captured by shifting the second grating 15.

FIG. 11a shows photographic schematic diagrams indicating images captured by shifting the second grating 15, when the subject is placed at subject placing plate 13. FIG. 11b shows photographic schematic diagrams indicating images captured by shifting the second grating 15, when no subject is placed at subject placing plate 13. FIG. 11c shows a photographic schematic diagram indicating an image that is restructured from the Moire images respectively captured in the five steps shown in FIG. 11a.

As you find when comparing the Moire images shown in FIG. 10a with those shown in FIG. 11a, the Moire images shown in FIG. 10b with those shown in FIG. 1 lb and the restructured image shown in FIG. 10c with that shown in FIG. 11c, even when the Moire images are captured by the first image capturing operations in which the multi slits element 12 is to be shifted, the image quality of each of the Moire images itself is not deteriorated, compared to that of each of the other Moire images captured by the second image capturing operations in which the second grating 15 is to be shifted, and further, since the relationship between the phases (periods) of the images is liable to be maintained, it is possible to acquire the restructured image equal to or better than that acquired by the second image capturing operations.

Although the image capturing experiment, abovementioned, has been performed by employing the horizontal-type X-ray image capturing apparatus, there is no difference between the horizontal-type and the vertical-type X-ray image capturing apparatuses, in regard to the fact that the substantially the same images can be obtained even by shifting the multi slits element, instead of the first grating or the second grating. In the conventional image capturing practice, there has been no such an idea (concept) that the multi slits element is made to move in order to obtain plural sheets of Moire images, but the concept (method) thereof has been restricted to such the configuration in which the first grating 14 or the second grating 15 is made to move. However, as a result of intensive considerations and experiments, the present inventors and the related members have finally revealed that even such the structural configuration, in which the multi slits element is made to move, makes it possible to obtain the substantially the same Moire images and the restructured image as those conventionally obtained. Further, the present inventors and the related members have made it possible to put the Talbot-Lau interferometer into practical use, by removing the high accurate moving mechanism from the peripheral area in the vicinity of the subject placing plate to which the patient approaches so as to eliminate the adverse impacts (adverse effects) on the image capturing operations, and by applying the abovementioned method to the vertical-type X-ray image capturing apparatus in which the optical elements are arranged in the vertical direction.

As described in the foregoing according to the present embodiment, the X-ray image capturing apparatus 1 is configured as the vertical-type apparatus in which the X-ray source 11, the multi slits element 12, the subject placing plate 13, the first grating 14, the second grating 15 and the X-ray detector 16 are arranged in the above-indicated order in the direction of gravitational force, and is provided with the driving section to move the multi slits element 12 in the x-direction. Every time when the multi slits element 12 moves at constant period intervals, the X-ray detector 16 repeats the processing for reading the image signals in response to the X-rays irradiated from the X-ray source 11, so as to obtain a plurality of Moire images captured at constant period intervals.

By introducing the structure for moving the multi slits element 12, instead of moving the second grating 15 (or the first grating 14), into the X-ray image capturing apparatus 1 serving as the vertical-type apparatus, it becomes unnecessary to provide the space, onto which the driving section for moving the second grating 15 is to be installed, in the vicinity of the second grating 15 that is disposed at a position nearer to the floor side than the subject. On the other hand, since the multi slits element 12, to which the driving section 12a is coupled, is disposed at a position in the vicinity of the X-ray source 11, it becomes possible to dispose only the structure, including the first grating 14, the second grating 15 and the X-ray detector 16, at a position in the vicinity of the feet of the patient without installing the driving mechanism, and it becomes possible to achieve such a structure in which the patient hardly contacts the driving mechanism or the apparatus proper. Since it is possible to rigidly structure the lower section, which is located below the subject and in which no driving mechanism is installed, even if a kind of vibration, caused by an unexpected contacting action of the patient, is transmitted to the X-ray image capturing apparatus 1, it becomes possible to prevent the X-ray image capturing apparatus 1 from generating the resonance or the like, and to impede the transmission of the vibration itself Therefore, it becomes possible to prevent the occurrence of such a case that the operator should wait for implementing the image forming operation until the vibration converges or the positional relationships between the multi slits element 12, the first grating 14 and the second grating 15 are fluctuated. Further, since the direction in which the patient approaches the subject placing plate is not restricted, it becomes possible to improve the flexibility of the image capturing operation. Accordingly, it becomes possible to provide such a vertical-type X-ray image capturing apparatus 1 that makes it possible not only to conduct the high-quality phase contrast image capturing operation, but also to sufficiently withstand the practical use as the practical vertical-type imaging apparatus.

Further, the multi slits element 12, the first grating 14 and the second grating 15 are integrally supported by the supporting member 17, and the positional relationship between the first grating 14 and the second grating 15 in the X-ray irradiating direction is fixed. Accordingly, it becomes possible to maintain the relative positional relationships between the related parts in the X-ray irradiating direction, caused by the impacts and vibrations occurring at the time of transporting and installing the X-ray image capturing apparatus 1. By maintaining the relative positional relationships abovementioned, it becomes possible to obtain the high-quality Moire images from the X-ray image capturing operations employing the Talbot-Lau interferometer, and as a result, it becomes possible to improve the reproducibility of the restructured image of the subject concerned, which is created from the high-quality Moire images above-obtained.

Still further, the X-ray detector 16, the first grating 14 and the second grating 15 are integrally supported by the supporting member 17, and the positional relationship between the first grating 14 and the second grating 15 in the X-ray irradiating direction is fixed. Accordingly, it becomes possible to maintain the positional relationships between the X-ray detector 16, the first grating 14 and the second grating 15. Generally speaking, since the position of the X-ray detector 16 is adjusted and disposed at such a position at which the Moire images formed by the second grating 15 do not blur, by maintaining the positional relationships abovementioned, it becomes possible to prevent the Moire images from generating the blurs caused by the fluctuation of the positional relationships.

In this connection, the abovementioned embodiment merely represents one of preferable examples embodied in the present invention, and the scope of the present invention is not limited to the embodiment abovementioned.

For instance, although the X-ray source 11, the multi slits element 12, the subject placing plate 13, the first grating 14, the second grating 15 and the X-ray detector 16 are arranged in this order (hereinafter, referred to as the first arrangement) in the abovementioned embodiment, even if the X-ray source 11, the multi slits element 12, the first grating 14, the subject placing plate 13, the second grating 15 and the X-ray detector 16 are arranged in this order (hereinafter, referred to as the second arrangement), it is possible to acquire the restructured image by moving the multi slits element 12 while the first grating 14 and the second grating 15 remain fixed onto supporting member 17.

In the second arrangement, since the center of subject is apart from the first grating 14 by the thickness of the subject, the sensitivity of the second arrangement would become inferior to that of the abovementioned embodiment. On the other hand, considering the reduction of dose of X-ray exposure onto the subject, you could find that the X-rays are effectively utilized in the second arrangement in regard to a part of the X-rays to be absorbed by the first grating 14, compared to that in the first arrangement.

Further, although the effective special resolution capability at the subject position depends on the diameter of the X-ray focal point, the special resolution capability of the detector, the subject enragement rate, the thickness of the subject, etc., when the special resolution capability of the detector employed in abovementioned embodiment is equal to or smaller than 120 μm (Gaussian half width), the effective special resolution capability of the second arrangement is smaller than that of the first arrangement.

It is preferable that the arrangement order of the first grating 14 and the subject placing plate 13 is determined by considering various kinds of factors, such as the sensitivity, the special resolution capability, the amount of X-rays to be absorbed by the first grating 14, etc.

Still further, it is applicable that a cable-less cassette type FPD (Flat Panel Detector), which incorporates a buttery so as to output the image signals to the main body section 18 in the wireless communication mode, is employed as the X-ray detector 16. By employing the cassette type FPD, it is possible to eliminate various kinds of cables to be coupled to the main body section 18, and accordingly, it becomes possible to further reduce the peripheral area around the X-ray detector 16. Then, the reduction of the concerned peripheral area makes it possible to widen the floor area under the feet of the subject, and as a result, to provide such the structure in which the patient hardly contact the X-ray detector 16, more hardly than ever.

Figure 12:
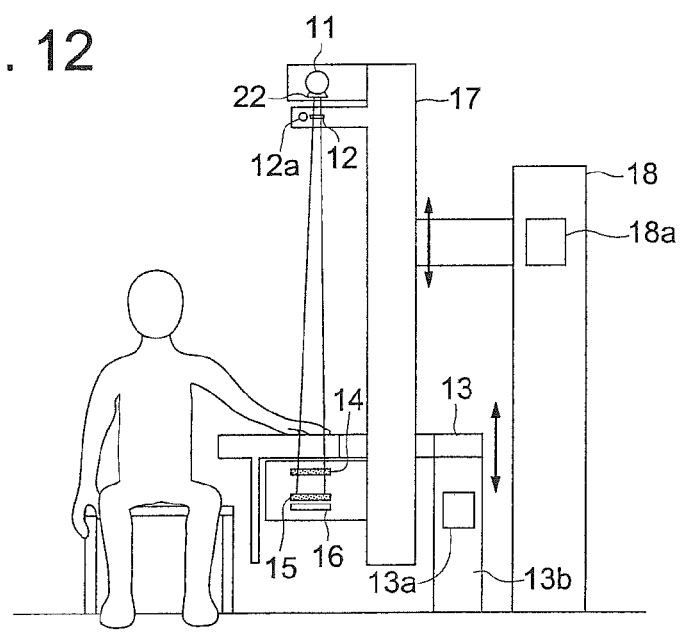
FIG. 12 shows a schematic diagram indicating a side view of an X-ray image capturing apparatus when a subject placing plate is supported by another supporting member, which is separated from a supporting member for supporting a first grating and a second grating.
Figure 13:
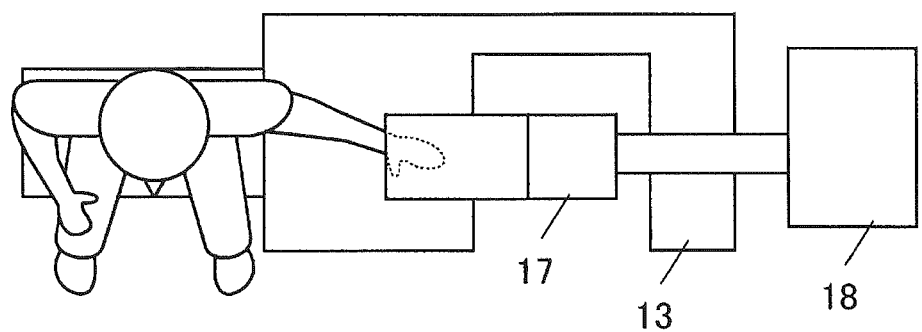
FIG. 13 shows a schematic diagram indicating a plane view of an X-ray image capturing apparatus shown in FIG. 12.

Still further, the subject placing plate 13 is liable to transmit the vibration caused by the contacting action between the patient and the subject placing plate 13. Accordingly, it is applicable that the subject placing plate 13 is made to separate from the supporting member 17 onto which the first grating 14, the second grating 15, etc. are fixed, so as to fix the subject placing plate 13 onto another supporting member. FIG. 12 shows a schematic diagram indicating a side view of the X-ray image capturing apparatus 1 when the subject placing plate 13 is supported by another supporting member 13b, while FIG. 13 shows a schematic diagram indicating a plane view of the same. As abovementioned, by making the subject placing plate 13 separate from the first grating 14, the second grating 15, etc., so as to configure it as the separate structure, it becomes possible to reduce the influence to be incurred by the positional relationships between the multi slits element 12, the first grating 14 and the second grating 15 as small as possible, and to maintain the positional relationships concerned.

When the subject placing plate 13 is configured as the separate structure, as shown in FIG. 12 and FIG. 13, a driving section 13a to move the subject placing plate 13 in the z-direction is incorporated in the supporting member 13b. The driving section 13a makes it possible to adjust the position of the subject placing plate 13 in conformity with the height of the subject. Although the body weight or the like of the patient is applied onto the subject placing plate 13, by making the subject placing plate 13 separate from the supporting member 17, it is possible to eliminate the load applied onto the supporting member 17 going up and down. Accordingly, it becomes unnecessary to reinforce the physical strength of the supporting member 17 so as to withstand the load to be applied onto subject placing plate 13, resulting in a cost reduction of the apparatus concerned.

Still further, in the abovementioned embodiment, described is such an example that the shifting and stopping actions of the multi slits element 12 are repeated for every image capturing step. However, when it can be assumed that, depending on the structure of the driving section 12a, the errors between the controlling amount and the actual moving amount are accumulated and expanded by repeating the shifting and stopping actions, and as a result, it is difficult to obtain the Moire images captured at constant intervals, it is preferable that the continuous image capturing method, in which a plurality of image capturing operations is implemented by continuously moving the multi slits element 12, is employed. Concretely speaking, when the exposure switch is turned ON, the multi slits element 12 starts moving. After the movement of the multi slits element 12 exceeds the unstable moving region at the initial activation transient, and enters into the stable moving region, the multi slits element 12 is further made to continuously move, so as to repeat the operations for irradiating X-ray pulse and reading the image signals for every predetermined shift amount (for instance, 4.56 μm).

It is preferable to employ such an X-ray tube that is capable of irradiating X-ray pulse, for the X-ray source 11 to be used in the continuous image capturing method.

Further, as the X-ray detector 16, it is preferable to employ such a FPD that has a large applicable frame rate (number of capturable image frames per unit time), and, preferably, is capable of shooting a movie image. When it is assumed that five times or more of the image capturing operations should be conducted within a time duration in a range of several hundred milliseconds—several seconds, it is necessary to set the frame rate at a value of at least 10 flames per second, and it is preferable to set the frame rate at a value being more than 10 flames per second.

In this connection, before the image capturing operation, the X-ray detector 16 is capable of performing an offset correction processing every step of the image capturing operations. In such the case that the image capturing time for each of the steps is too short to perform the offset correction processing it is applicable that the operation for reading the dark offset data is conducted only at the initial step of the image forming operation to acquire the offset correction value so as to apply the concerned offset correction value to all of the image capturing operations in the later steps. Alternatively, it is also applicable that, after the consecutive image capturing operations have been completed, the operation for reading the dark offset data is conducted to acquire the offset correction value, so as to commonly apply the concerned offset correction value to the image capturing operations implemented in the all steps.

In the case of the continuous image capturing method, it is applicable that the pre-shooting operations are conducted before and after each of the image capturing steps concerned.

When the driving section 12a could drive the movement of the multi slits element 12 with an ideal transporting accuracy, namely, when the multi slits element 12 could move at a constant moving velocity, the Moire images respectively acquired in the image capturing steps can form the sine wave indicated in the graph shown in FIG. 7. However, if deviations of the transporting amount, caused by various kinds of factors, such as an aging change, a backlash of the driving section 12a, an influence of inertia at the time of activation, etc., have been generated, it is impossible to obtain the Moire images at the constant period intervals. For instance, as shown in FIG. 7, although the Moire image at the third step should correspond to that at 0.4 period serving as the originally intended value, if the transporting amount at the time of the third step deviates from the originally intended value, the Moire image at the time before or after 0.4 period is actually acquired.

As abovementioned, when the periods of the Moire images at the image capturing steps concerned vary from the originally intended values, it is impossible to calculate accurate phases, and as a result, it is impossible to accurately reproduce the subject image serving as the restructured image. To overcome such the drawback, for instance, in addition to the normal image capturing operations to be respectively conducted at the image capturing times of 2, 4, 6, 8 and 10 seconds, the backup image capturing operations are respectively conducted at the image capturing times ±0.1 seconds, so that the total 15 times of the image capturing operations are conducted. Accordingly, since the three Moire images are respectively obtained at the image capturing times of 1.9, 2.0 and 2.1 seconds in the first step, and three sheets of Moire images can be obtains at each of the steps, a set of Moire images, which exhibits such a sine curve that is most approximate to the ideal sine curve of the X-ray relative intensity, is selected from plural sets of the Moire images above-obtained, so as to employ it for constructing the restructured image. According to this method, even if some error is generated in the transportation amount of the driving section 12a, it becomes possible to improve the reproducibility of the restructured image.

The time of ±0.1 seconds, cited as the adjusting time for the backup image capturing operation in the above, is merely an exemplified value, and it is applicable that the adjusting time may be determined as needed by implementing the test image capturing operation. For instance, it is applicable that, at the time when the X-ray image capturing apparatus 1 is installed, the test image capturing operations are implemented several times by changing the adjusting time for the backup image capturing operation around before and after the image capturing operation to be conducted in each of the steps, such as ±0.1 seconds, ±0.2 seconds, etc., so as to find such an adjusting time that is most liable to match with the sine curve concerned. As a result, it becomes possible to cope with such a case that the necessary adjusting time differs depending on the device characteristics of the driving section 12a.

When the X-ray tube incorporated in the X-ray source 11, which is to be used in the continuous image capturing method, is not capable of irradiating the X-ray pulse, it is applicable that a shutter 22 is disposed at a position in the vicinity of the X-ray irradiation opening of the X-ray source 11 as shown in FIG. 12. Although it is applicable that a general purpose shutter mechanism, which is to be equipped in the camera or the like, is employed as the shutter 22, it is also applicable that the shutter 22 is configured as such a mechanism that is exemplified by the schematic diagram shown in FIG. 14, and is provided with a function for adjusting the irradiation field aperture.

Figure 14:
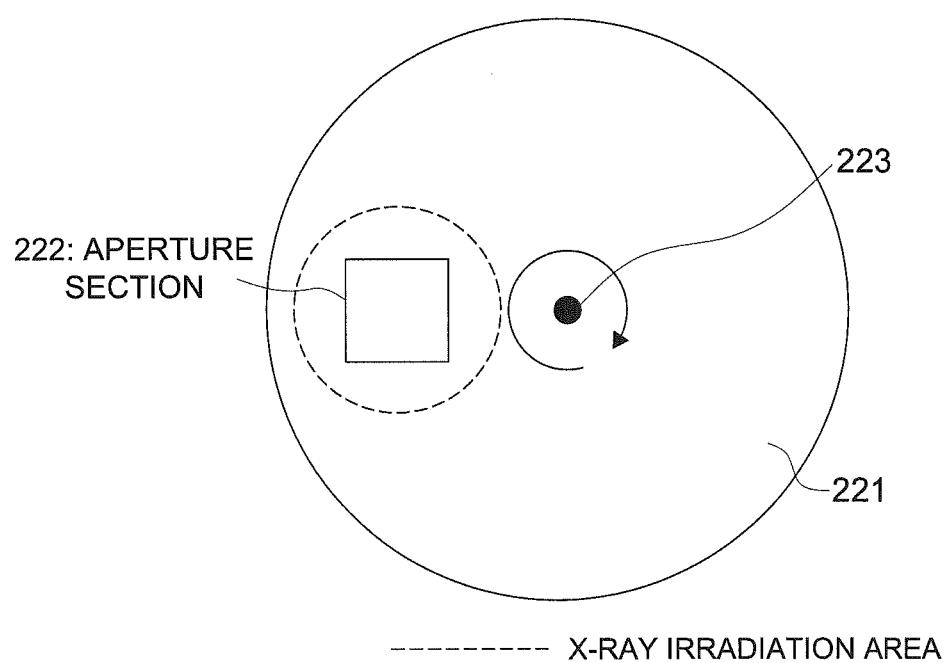
FIG. 14 shows a schematic diagram indicating an example of a shutter.

As shown in FIG. 14, the shutter 22 is constituted by an X-ray shielding section 221 formed in a circular disc shape and an aperture section 222 formed therein. During the time when the X-ray shielding section 221 shields the X-ray irradiation area of the X-ray source 11 while the X-ray shielding section 221 is rotating around a rotation axis 223, the shutter 22 is kept at the closed state. On the other hand, during the time when the area of the aperture section 222 overlaps with that of the X-ray irradiation area of the X-ray source 11, the shutter 22 is kept at the open state, and the X-rays are irradiated through the aperture section 222. As abovementioned, the opening and closing actions conducted by the shutter 22 make it possible to perform the operation for irradiating the X-ray pulse, being similar to that performed by the X-ray tube capable of irradiating X-ray pulse by itself The aperture section 222 also serves as an aperture adjusting mechanism so as to make it possible to adjust the irradiation field of the X-rays by adjusting the opening area of the aperture section 222.

Figure 15:
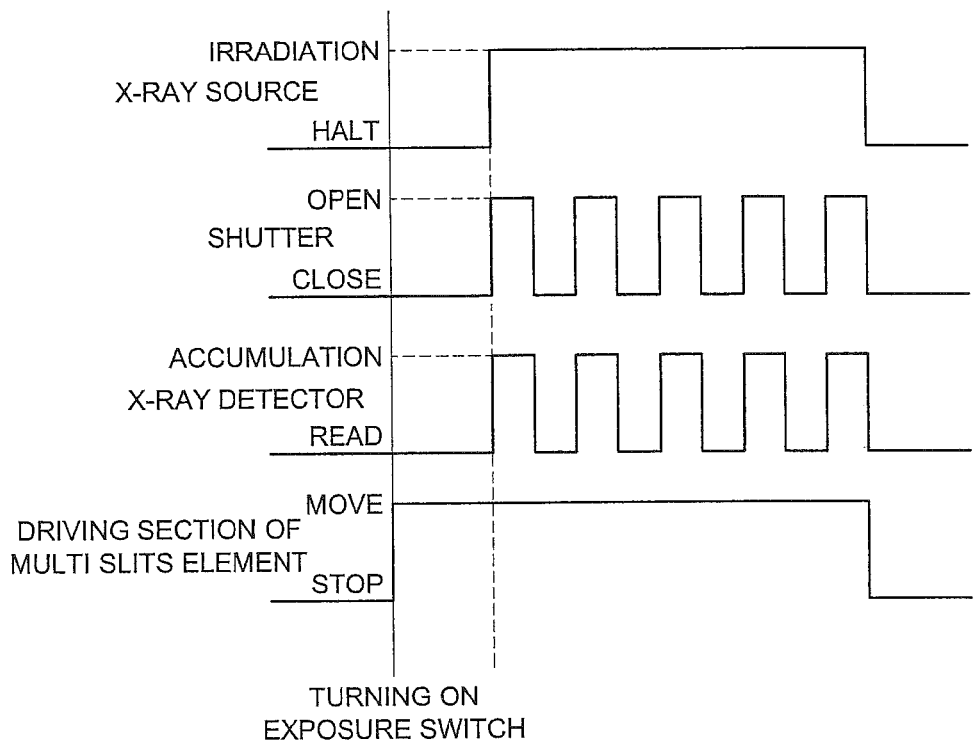
FIG. 15 shows a schematic diagram indicating relationships between timing charts of actions to be respectively conducted by an X-ray source, a shutter, an X-ray detector and a driving section of a multi slits element, when the shutter is employed for implementing image capturing operations.

The rotating velocity of the shutter 22 is adjusted at such a velocity that makes the shutter 22 perform the opening and closing actions in synchronization with the image capturing intervals of the five steps. FIG. 15 shows a schematic diagram indicating relationships between timing charts of the actions to be conducted by the X-ray source 11, the shutter 22, the X-ray detector 16 and the driving section 12a, when the continuous image capturing operations of the five steps are implemented. As shown in FIG. 15, when the exposure switch is turned ON, the driving section 12a commences the operation for moving the multi slits element 12, and then, after a predetermined time has elapsed, the X-ray source 11 commences the X-ray irradiating operation. At the same time when the X-ray irradiating operation is commenced, the shutter 22 is opened, and the X-ray detector 16 implements the operation for accumulating electric charges therein. After a predetermined time has elapsed, the shutter 22 is closed, and, synchronizing with the shutter closed timing the electric charges accumulated by the X-ray detector 16 are read out as the image signals. Through the abovementioned process, the X-ray detector 16 repeats the operations for accumulating the electric charges and for reading out the image signals five times corresponding to the five image capturing steps, in synchronization with the opening and closing actions of the shutter 22. At the time when the five image capturing steps have been completed, the X-ray source 11 halts the operation for irradiating the X-rays, and the rotating action of the shutter 22 is deactivated so as to halt the opening and closing actions of the shutter 22 as well Further, the X-ray detector 16 also halts the operation for accumulating the electric charges and for reading out the image signals.

<Other Embodiment>

The X-ray image capturing apparatus 1, described in the foregoing as the embodiment of the present invention, has such the configuration that is to be exclusively used (available) for the image capturing operation conducted by the Talbot-Lau interferometer. However, depending on the medical facility, sometimes, there has been such a case that the X-ray source to be used for a conventional X-ray image capturing operation is equipped at the ceiling section in advance, or the subject placing plate is fixed onto the floor in advance. If the X-ray image capturing apparatus 1 were introduced into such the environment as abovementioned, it would be impossible to effectively use the existing X-ray image capturing devices already installed therein. To overcome such the problem, an exemplary X-ray image capturing apparatus, which is available for performing both the normal (conventional) image capturing operation and the novel image capturing operation that employs the Talbot-Lau interferometer, will be detailed in the following as another embodiment of the present invention.

Figure 16:
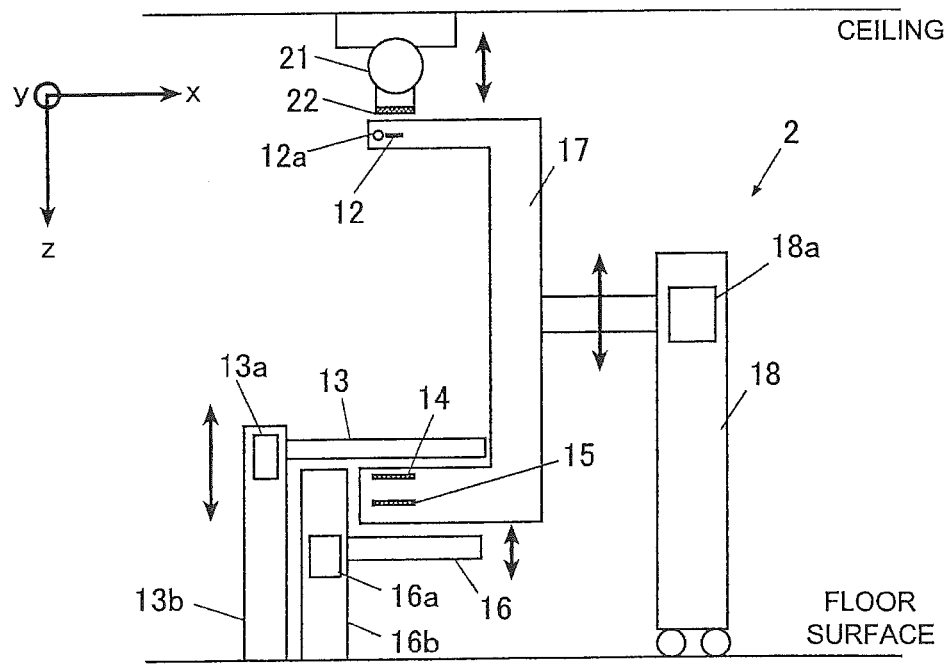
FIG. 16 shows a schematic diagram indicating a side view of an X-ray image capturing apparatus embodied in the present invention as another embodiment.

FIG. 16 shows a schematic diagram indicating a side view of an X-ray image capturing apparatus 2 embodied in the present invention as another embodiment. In the X-ray image capturing apparatus 2, the same reference number is attached to the structural element being same as that of the X-ray image capturing apparatus 1. As shown in FIG. 16, the X-ray image capturing apparatus 2 is constituted by the X-ray source 21, the subject placing plate 13 and the X-ray detector 16, each of which is configured separately from the other structural elements. Further, the multi slits element 12, the first grating 14 and the second grating 15 are supported by the supporting member 17, so as to fix the positional relationships between them in the X-ray irradiating direction (z-direction). Still further, the wheels are attached to the lower section (bottom surface) of the main body section 18, so as to make it possible to freely move the position of the main body section 18 and the supporting member 17.

The X-ray source 21, the subject placing plate 13 and the X-ray detector 16 are installed in advance into the medical facility concerned, as the existing X-ray image capturing devices. The X-ray source 21 is equipped on the ceiling section in such a manner that the X-ray source 21 is movable in the z-direction. While the subject placing plate 13 and the X-ray detector 16 are supported by the supporting member 13b and a supporting member 16b, respectively, and the driving section 13a and a driving section 16a make it possible to move the subject placing plate 13 and the X-ray detector 16 in the z-direction, respectively.

In the X-ray image capturing apparatus 2, for instance, the multi slits element 12, the first grating 14 and the second grating 15 can be configured as described in the following.

Under the conditions of Diameter of a focal point of the X-ray tube: 600 μm, Tube voltage: 40 kVp, Additional filter: aluminum 16 mm, Distance "d1" from the focal point of the X-ray source 21 to the multi slits element 12: 240 mm, Distance "d3" from the multi slits element 12 to the first grating 14: 1690 mm, Distance "d3+d4" from the multi slits element 12 to the second grating 15: 1990 mm, Size of the multi slits element 12: 10 square-mm, Slit period: 30 μm, Size of the first grating 14: 50 square-mm, Slit period: 4.5 μm, Size of the second grating 15: 50 square-mm, Slit period: 5.3 μm.

When the X-ray image capturing operation is implemented by employing the Talbot-Lau interferometer, the subject placing plate 13 is moved at first, so as to adjust its height to the height position of the subject, as shown in FIG. 16. Successively, the X-ray detector 16 is moved so as to make it apart from the subject placing plate 13, and then, the main body section 18 is moved so as to insert the first grating 14 and the second grating 15 into a gap space formed between the subject placing plate 13 and the X-ray detector 16, and after that, the positions of them are fixed. Still successively, the position of the supporting member 17 is moved so as to make the first grating 14 approach the subject placing plate 13. Yet successively, the position of the X-ray detector 16 is moved so as to make the X-ray detector 16 approach the second grating 15, and the X-ray source 21 is moved so as to make the X-ray source 21 approach the multi slits element 12.

Figure 17:
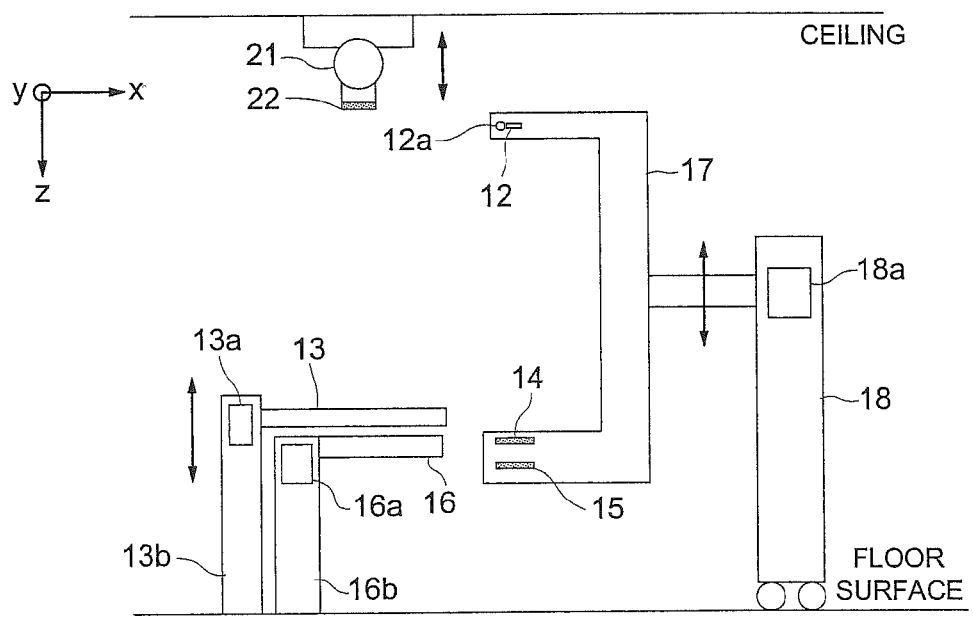
FIG. 17 shows a schematic diagram indicating a conventional X-ray image capturing mode to be implemented by employing an X-ray image capturing apparatus shown in FIG. 15.

On the other hand, when the X-ray image capturing operation is implemented according to the conventional method, the main body section 18 is made to move so as to remove the supporting member 17 from the gap space formed between the subject placing plate 13 and the X-ray detector 16, as shown in FIG. 17. Herein, the X-ray image capturing operation according to the conventional method as abovementioned is equivalent to that according to the absorption-contrast X-ray method, serving as a kind of closely-contacted image capturing operation in which the subject and the X-ray detector 16 are arranged at such positions that are closely contacted with each other. Accordingly, after the supporting member 17 has been removed, the subject placing plate 13 is moved to such a position that is in conformity with the height position of the subject, and then the X-ray detector 16 is moved so as to make the X-ray detector 16 closely contact with the subject placing plate 13.

Figure 18:
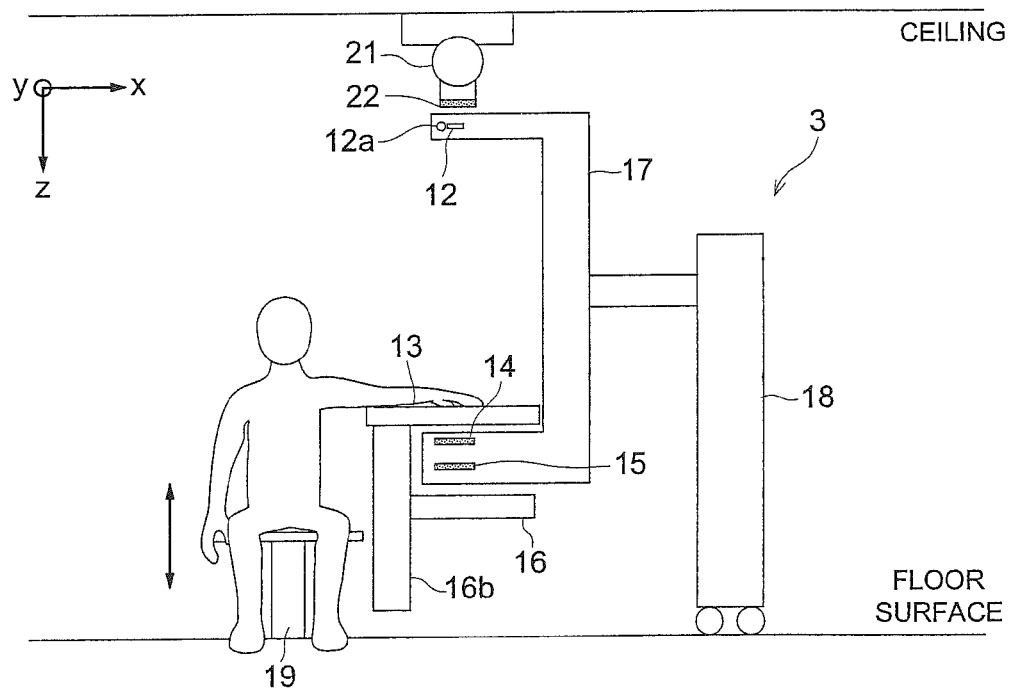
FIG. 18 shows a schematic diagram indicating a side view of an X-ray image capturing apparatus embodied in the present invention as another embodiment.

In this connection, when the image capturing subject is the fingers of patient's hand or the like as indicated in the schematic diagram including an X-ray image capturing apparatus 3 shown in FIG. 18, considering that even a patient of relatively advanced age can move his fingers in up and down directions, it is applicable that the X-ray image capturing apparatus is so constituted that the position of the subject placing plate 13 is fixed, and a chair-type lifting table 19 is provided so as to move the position of the patient in the up and down directions. According to this configuration, it becomes possible to omit such a labor that is required for adjusting the positions of the X-ray source 21, the subject placing plate 13 and the X-ray detector 16, and it is not necessary to provide the driving mechanism for moving up and down the supporting member 17. In addition, by moving the position of the chair-type lifting table 19 in the up and down directions so as to make a contacting area, at which the patient contacts the subject placing plate 13, as larger as possible, it becomes possible to stabilize the position of the subject. For instance, after the patient has put his hand, serving as the subject concerned, on the subject placing plate 13, the position of the chair-type lifting table 19 is moved downward so as to make not only the hands, but also the arm portion contact the subject placing plate 13. By also making the arm portion place thereon, it becomes possible to stabilize the position of the subject (hand portion) put on the subject placing plate 13, and as a result, it becomes possible to prevent the subject form unexpectedly moving at the time of the image capturing operation thereof In this connection, it is also applicable that the X-ray image capturing apparatus 3 is so constituted that the X-ray detector 16 is fixed onto the supporting member 17.

As abovementioned, the X-ray image capturing apparatus 2 or 3 can be constituted by employing the X-ray source 21, the subject placing plate 13 and the X-ray detector 16, which serve as the currently-existing devices at the installation place concerned. In the present embodiment, it is also possible that the multi slit element (including the driving mechanism for moving use) is disposed at the existing tube (including a collimator) side, while, the first grating, the second grating and the X-ray detector are constituted as a grating unit being separate from the multi slit element, so as to adjust the position of the concerned grating unit relative to the tube+the multi slit element side at the time of installing the apparatus concerned. Although the large-scale integrated apparatus arises the difficulty at the time of transporting it, according to the abovementioned case, by dividing the apparatus into a plurality of units, the dimensions of each unit becomes minimized, and as a result, it becomes possible to drastically improve the transportability thereof.

In this connection, depending on the characteristics of the X-ray image capturing apparatus, specifically depending on the tube characteristics, it is assumed that each of the image capturing intervals for capturing the consecutive Moire images (in the aforementioned embodiment, the five sheets of Moire images acquired by the image capturing operations in the five steps), which are to be employed for creating the restructured image, is set at a value in a range of several seconds through even several minutes. In this case, it is possible to conduct the image capturing operation by employing the CR cassette that incorporates the stimulus phosphor sheet. It becomes possible to configure such a system in which the image capturing operator, such as a technician or the like, changes the exposed CR cassette to new one and loads the exposed CR cassette onto the reading device so as to transmit the read image data to the controller 5, until the next image capturing operation becomes possible.

According to the present invention, the following effects can be attained.

(1) In the X-ray image capturing apparatus that employs the Talbot-Lau interferometer, it becomes possible to make the structural arrangement of the detecting system to be disposed in the vicinity of the subject constitute only the first grating, the second grating and the X-ray detector, without providing the shift-use driving system for changing the relative positional relationship between the first grating and the second grating. According to the abovementioned compactifying technique, fundamentally, it becomes possible to achieve such a structure in which the patient hardly contacts the structural section of the detecting system disposed in the vicinity of the subject placing plate of the X-ray image capturing apparatus. Since it is possible to rigidly structure the structural section of the detecting system to be disposed in the vicinity of the subject placing plate, even if a kind of vibration, caused by an unexpected contacting action of the patient, is transmitted to the X-ray image capturing apparatus, it becomes possible to prevent the X-ray image capturing apparatus from generating the resonance or the like, and to impede the transmission of the vibration itself Therefore, it becomes possible to prevent the occurrences of such a case that the operator should wait for implementing the image forming operation until the vibration converges and/or the positional relationships between the multi slits element, the first grating and the second grating, for which accurate positional adjustments are required, are fluctuated by the vibrations. Specifically, when the X-ray image capturing apparatus is structured as a vertical-type configuration, it becomes possible to promote the minimization of the area for installing the apparatus concerned, and at the same time, since the direction in which the patient approaches the subject placing plate is not restricted, it becomes possible to improve the flexibility of the image capturing operation.

(2) Accordingly, it becomes possible to provide such a vertical-type X-ray image capturing apparatus that makes it possible not only to conduct the high-quality phase contrast image capturing operation, but also to sufficiently withstand the practical use as the practical vertical-type imaging apparatus.

(3) Further, according to the image creating method embodied in the present invention, it becomes possible to acquire such a reconstructed image of the subject that is more accurate than that acquired by the conventional-type Talbot-Lau interferometer, or it becomes possible to alleviate the demands for the accuracy (specifically, in regard to the activation and deactivation characteristics) of the driving mechanism (including the driving source and the reduction transmission system), which is indispensable for the relative positional moving use, resulting in an improvement of the flexibility of apparatus design and a cost reduction of the parts constituting the driving mechanism concerned.

The invention claimed is:

1. An X-ray image capturing apparatus, comprising:
   an X-ray source that emits X-rays to be irradiated onto a subject;
   a plurality of gratings;
   a driving section that moves at least one of the plurality of gratings;
   an X-ray detector in which conversion elements to convert intensities of X-rays received thereby to electric signals are arranged in a two-dimensional pattern;
   a subject placing plate on which the subject is to be placed;
   a first supporting member that supports the X-ray source, the plurality of gratings and the X-ray detector; and
   a second supporting member that supports the subject placing plate;
   wherein the first supporting member is out of contact with the second supporting member.

2. The X-ray image capturing apparatus of claim 1, wherein the X-ray source, the plurality of gratings, the subject placing plate and the X-ray detector are aligned in a vertical direction relative to a floor surface.

3. The X-ray image capturing apparatus of claim 2, further comprising:
   a multi slits element that has a plurality of slits and is disposed at the X-ray source;
   wherein the first supporting member also supports the multi slits element.

4. The X-ray image capturing apparatus of claim 3, wherein the driving section drives the multi slits element to move.

5. The X-ray image capturing apparatus of claim 2, further comprising:
   a support member driving section that moves the first supporting member and the second supporting member in up and down directions, respectively.

6. An X-ray image capturing apparatus, comprising:
   an X-ray source that emits X-rays to be irradiated onto a subject;
   a plurality of gratings;
   a driving section that moves at least one of the plurality of gratings;
   an X-ray detector in which conversion elements to convert intensities of X-rays received thereby to electric signals are arranged in a two-dimensional pattern;
   a subject placing plate on which the subject is to be placed;
   a first supporting member that supports the plurality of gratings and the X-ray detector; and
   a second supporting member that supports the subject placing plate;
   wherein the first supporting member is out of contact with the second supporting member.

7. The X-ray image capturing apparatus of claim 6, wherein the X-ray source, the plurality of gratings, the subject placing plate and the X-ray detector are aligned in a vertical direction relative to a floor surface.

8. The X-ray image capturing apparatus of claim 7, further comprising:
   a multi slits element that has a plurality of slits;
   wherein the first supporting member also supports the multi slits element.

9. The X-ray image capturing apparatus of claim 7, further comprising:
   wherein the first supporting member is movable in at least one of an x-direction, a y-direction and a z-direction.

* * * * *